(12) United States Patent
Zwicker et al.

(10) Patent No.: US 11,872,241 B2
(45) Date of Patent: Jan. 16, 2024

(54) COMPOSITIONS AND METHODS FOR REDUCING MAJOR THROMBOTIC EVENTS IN CANCER PATIENTS

(71) Applicant: Beth Israel Deaconess Medical Center, Inc., Boston, MA (US)

(72) Inventors: Jeffrey I. Zwicker, Boston, MA (US); Bruce Furie, Boston, MA (US); Jack Davis Stopa, Boston, MA (US); Robert Flaumenhaft, Boston, MA (US)

(73) Assignee: BETH ISRAEL DEACONESS MEDICAL CENTER, INC., Boston, MA (US)

( * ) Notice: Subject to any disclaimer, the term of this patent is extended or adjusted under 35 U.S.C. 154(b) by 0 days.

(21) Appl. No.: 16/696,280

(22) Filed: Nov. 26, 2019

(65) Prior Publication Data

US 2020/0171064 A1   Jun. 4, 2020

Related U.S. Application Data

(60) Provisional application No. 62/773,696, filed on Nov. 30, 2018.

(51) Int. Cl.
| | |
|---|---|
| *A61K 31/7048* | (2006.01) |
| *A61K 31/352* | (2006.01) |
| *A61P 35/04* | (2006.01) |
| *A61K 31/375* | (2006.01) |
| *A61K 31/519* | (2006.01) |
| *A61K 31/45* | (2006.01) |

(52) U.S. Cl.
CPC ........ *A61K 31/7048* (2013.01); *A61K 31/352* (2013.01); *A61K 31/375* (2013.01); *A61K 31/45* (2013.01); *A61K 31/519* (2013.01); *A61P 35/04* (2018.01)

(58) Field of Classification Search
None
See application file for complete search history.

(56) References Cited

U.S. PATENT DOCUMENTS

| | | | |
|---|---|---|---|
| 3,840,950 A | 10/1974 | Stanley et al. | |
| 4,871,718 A | 10/1989 | Carniglia | |
| 5,026,721 A | 6/1991 | Dudrick et al. | |
| 5,578,590 A | 11/1996 | Grunicke et al. | |
| 5,626,884 A | 5/1997 | Lockett | |
| 5,804,594 A | 9/1998 | Murad | |
| 5,846,569 A | 12/1998 | Anderson et al. | |
| 5,948,443 A | 9/1999 | Riley et al. | |
| 6,103,756 A | 8/2000 | Gorsek | |
| 6,121,249 A | 9/2000 | Weissman et al. | |
| 6,203,818 B1 | 3/2001 | Vester | |
| 6,210,701 B1 | 4/2001 | Darland et al. | |
| 6,261,589 B1 | 7/2001 | Pearson et al. | |
| 6,277,426 B1 | 8/2001 | Reust | |
| 6,277,427 B1 | 8/2001 | Husz | |
| 6,299,925 B1 | 10/2001 | Xiong et al. | |
| 6,352,712 B1 | 3/2002 | Ukaczer et al. | |
| 6,420,142 B1 | 7/2002 | Buchholz et al. | |
| 6,458,406 B1 | 10/2002 | Ono et al. | |
| 6,491,948 B1 | 12/2002 | Buchholz et al. | |
| 6,511,675 B2 | 1/2003 | Siddiqui et al. | |
| 6,514,527 B1 | 2/2003 | Buchholz et al. | |
| 6,514,973 B1 | 2/2003 | Buchholz et al. | |
| 6,541,062 B2 | 4/2003 | Ono et al. | |
| 6,551,629 B1 | 4/2003 | Gorsek | |
| 6,579,544 B1 | 6/2003 | Rosenberg et al. | |
| 6,616,959 B2 | 9/2003 | Ono et al. | |
| 6,683,164 B1 | 1/2004 | Buchholz et al. | |
| 6,812,215 B2 | 11/2004 | Buchholz et al. | |
| 6,821,536 B2 | 11/2004 | Lines et al. | |
| 7,009,062 B2 | 3/2006 | Buchholz et al. | |
| 7,041,652 B1 | 5/2006 | Buchholz et al. | |
| 7,182,972 B2 | 2/2007 | Ono et al. | |
| 7,270,840 B2 | 9/2007 | Lines et al. | |
| 7,588,733 B2 | 9/2009 | Rich et al. | |
| 7,745,486 B2 | 6/2010 | Lines | |
| 7,943,662 B2 | 5/2011 | Carolo et al. | |
| 7,960,430 B2 | 6/2011 | Wirth et al. | |
| 8,680,053 B2 | 3/2014 | Lines | |
| 10,391,096 B2 | 8/2019 | Lines | |
| 2002/0025350 A1 | 2/2002 | Siddiqui et al. | |
| 2002/0151599 A1 | 10/2002 | Buchholz et al. | |
| 2003/0054357 A1 | 3/2003 | Young et al. | |
| 2003/0068391 A1 | 4/2003 | Harris et al. | |
| 2004/0101595 A1 | 5/2004 | Lines et al. | |
| 2004/0126461 A1 | 7/2004 | Lines et al. | |
| 2005/0031737 A1 | 2/2005 | Lines et al. | |
| 2005/0266121 A1 | 12/2005 | Lines et al. | |
| 2006/0003947 A1 | 1/2006 | Udell | |

(Continued)

FOREIGN PATENT DOCUMENTS

| | | |
|---|---|---|
| CN | 1507870 A | 6/2004 |
| CN | 1562096 A | 1/2005 |

(Continued)

OTHER PUBLICATIONS

Ay, Blood, Oct. 1, 2008, vol. 112, No. 7, pp. 2703-2708. (Year: 2008).*
Shamay, Sci Transl Med. Jun. 2, 20169; 8(345):345ra87. (Year: 2016).*
Oh, Evidence-Based Complementary and Alternative Medicine, vol. 2012, Article ID 485262, 10 pages. (Year: 2012).*
Sheth, Cardiovascular Diagnosis and Therapy, vol. 7, Suppl Dec. 3, 2017. (Year: 2017).*
Baaten et al. "A Synthesis Approach of a Mouse Studies to Identify Genes and Proteins in Arterial Thrombosis and Bleeding" Dec. 13, 2018, Blood 132(24):e35-e46.
International Search Report and Written Opinion for PCT/US2020/064101 dated Mar. 4, 2021.
Razak et al. "Cancer-Associated Thrombosis: an Overview of Mechanisms, Risk Factors, and Treatment" 2018, Cancers 10(380):1-21.

(Continued)

*Primary Examiner* — Layla D Berry
(74) *Attorney, Agent, or Firm* — DLA PIPER (US) LLP

(57) ABSTRACT

The present invention relates to methods for reducing soluble P-selectin and major thrombotic events in cancer patients.

28 Claims, 6 Drawing Sheets

(56) References Cited

U.S. PATENT DOCUMENTS

| | | | |
|---|---|---|---|
| 2006/0276393 | A1 | 12/2006 | Milburn et al. |
| 2007/0148210 | A1 | 6/2007 | Lines et al. |
| 2007/0248590 | A1 | 10/2007 | Milne et al. |
| 2008/0032987 | A1 | 2/2008 | Lines |
| 2009/0163448 | A1 | 6/2009 | Powell |
| 2011/0224290 | A1 | 9/2011 | Estrela Ariquel et al. |
| 2013/0020864 | A1 | 1/2013 | Smajlovic et al. |
| 2013/0028864 | A1 | 1/2013 | Theoharides |
| 2013/0095095 | A1 | 4/2013 | Lines |
| 2013/0129680 | A1 | 5/2013 | Lines |
| 2014/0350129 | A1 | 11/2014 | Sikora et al. |
| 2015/0366838 | A1* | 12/2015 | Lines ............. A61K 31/675 424/134.1 |
| 2016/0028759 | A1 | 1/2016 | Lorence et al. |
| 2016/0041153 | A1 | 2/2016 | Brown et al. |
| 2016/0287591 | A1 | 10/2016 | Lorence et al. |
| 2019/0241633 | A1 | 8/2019 | Fotin-Mleczek et al. |
| 2019/0336473 | A1 | 11/2019 | Lines |
| 2023/0029216 | A1 | 1/2023 | Zwicker et al. |

FOREIGN PATENT DOCUMENTS

| | | |
|---|---|---|
| CN | 1706466 A | 12/2005 |
| CN | 1715277 A | 1/2006 |
| CN | 1895264 A | 1/2007 |
| CN | 101554379 A | 10/2009 |
| CN | 100581552 C | 1/2010 |
| CN | 101623295 A | 1/2010 |
| DE | 102006036307 A1 | 2/2008 |
| JP | 200251732 A1 | 2/2002 |
| JP | 2002293711 A1 | 10/2002 |
| JP | 2006503896 A | 2/2006 |
| JP | 2006507283 A | 3/2006 |
| WO | 9841195 A2 | 9/1998 |
| WO | 0012085 A1 | 3/2000 |
| WO | 2000028986 A1 | 5/2000 |
| WO | 0207768 A1 | 1/2002 |
| WO | 2003007846 A1 | 1/2003 |
| WO | 2004037015 A1 | 5/2004 |
| WO | 2005095651 A2 | 10/2005 |
| WO | 2005117924 A1 | 12/2005 |
| WO | 2006076681 A2 | 7/2006 |
| WO | 2006084142 A2 | 8/2006 |
| WO | 2008011363 A2 | 1/2008 |
| WO | 2008011364 A2 | 1/2008 |
| WO | 2009025790 A1 | 2/2009 |
| WO | 2010078945 A2 | 7/2010 |
| WO | 2010119001 A1 | 10/2010 |
| WO | 2011042482 A1 | 4/2011 |
| WO | 2013055679 A2 | 4/2013 |
| WO | 2014070868 A1 | 5/2014 |
| WO | 2014111268 A1 | 7/2014 |
| WO | 2015125137 A1 | 8/2015 |
| WO | 2015196036 A1 | 12/2015 |
| WO | 2017027379 A1 | 2/2017 |
| WO | 2017083281 A1 | 5/2017 |
| WO | 2018170457 A1 | 9/2018 |
| WO | 2023288044 A1 | 1/2023 |

OTHER PUBLICATIONS

Zangari et al. "Increased risk of deep-vein thrombosis in patients with multiple myeloma receiving thalidomide and chemotherapy" Sep. 1, 2001, Blood 98(5):1614-1615.

Zhang et al. "Linking inflammation and thrombosis: Role of C-reactive protein" Nov. 26, 2010, World J Cardiol. 2 (11):365-369.

Angst et al. "The Flavonoid Quercetin Inhibits Pancreatic Cancer in Vitro and in Vivo" 2013, Pancreas 42(2):223-229.

Bucek et al. "C-reactive protein in the diagnosis of deep vein thrombosis" 2002, British Journal of Haematology 119:385-389.

Chou "Theoretical Basis, Experimental Design, and Computerized Simulation of Synergism and Antagonism in Drug Combination Studies" 2006, Pharmacol Rev 58:621-681.

Chow et al. "Phase I Pharmacokinetic Study of Tea Polyphenols Following Single-dose Administration of Epigallocatechin Gallate and Polyphenon E" 2001, Cancer Epidemiology, Biomarkers & Prevention 10:53-58.

Conuz et al. "Importance of Findings on the Initial Evaluation for Cancer in Patients with Symptomatic Idiopathic Deep Venous thrombosis" 1996, Ann Intern Med. 125(10):785-793.

Cortellaro et al. "The Plat Study: Hemostatic Function in Relation to Atherothrombotic Ischemic Events in Vascular Disease Patients Principal results" 1992, Arteriosclerosis and Thrombosis 12:1063-1070.

Crespy et al. "Quercetin, but not Its Glycosides, Is Absorbed from the Rat Stomach" 2002, Journal of Agricultural and Food Chemistry 50:68-621.

DiLorenzo et al. "Complete Response and Fatigue Improvement With the Combined Use of Cyclophosphamide and Quercetin in a Patient with Metastatic Bladder Cancer" Feb. 2016, Medicine 95(5):1-4.

DiSanto et al. "Resveratrol and Quercetin Down-Regulate Tissue Factor Expression by Human Stimulated Vascular Cells" 2003, Journal of Thrombosis and Haemostasis 1:1089-1095.

Dulloo et al. "Efficacy of Green Tea Extract Rich in Catechin Polyphenals and Caffeine in Increasing 24-h Energy Expenditure and Fat Oxidation in Humans 1-3" 1999, Am. J. Clin. Nutr. 70:1040-1045.

Edwards et al. "Quercetin Reduces Blood Pressure in Hypertensive Subjects" 2007, J. Nutr. 137:2405-2411.

Erlund et al. "Pharmacokinetics of Quercetin from Quercetin Aglycone and Rutin in Healthy Volunteers" 2000, Eur. J. Clin. Pharmacol. 56:545-553.

European Supplemental Search Report and Written Opinion for EP 07799611 dated Mar. 15, 2011.

European Supplemental Search Report and Written Opinion for EP 15810201 dated May 15, 2018.

Feldman et al. "Intravascular hemodynamic factors esponsible for progression of coronary atherosclerosis and development of vulnerable plaque" 2000, Current Opinion in Cardiology 15:430-440.

Fennerty "Venous thromboembolic disease and cancer" 2006, Postgrad Med J. 82:642-648.

Gill et al. "Human C-Reactive Protein Increases Cerebral Infarct Size After Middle Cerebral Artery Occlusion in Adult Rats" 2004, Journal of Cerebral Blood Flow & Metabolism 24:1214-1218.

Guardia et al. "Anti-Inflammatory Properties of Plant Flavinoids. Effect of Rutin, Quercetin and Hesperidin on Adjuvant Arthritis in Rat" 2001, Il Farmaco 56: 683-687.

Guo et al. "Subsequent Chemotherapy Reverses Acquired Tyrosine Kinase Inhibitor Resistance and Restores Response to Tyrosine Kinase Inhibitor in Advanced Non-Small-Cell Lung Cancer" 2011, BMC Cancer 11:90.

Harwood et al. "A critical review of the data related to the safety of quercetin and lack of evidence of in vivo toxicity, Including lack of genotoxic carcinogenic properties" 2007, Food and Chemical Toxicology 45:2179-2205.

Braheim et al. "Combined Cyclophosphomide Chemotherapy and Maltose Tetrapalmitate Immunotherapy in the Treatment of Transplanted Bladder and Prostate Carcinoma of the Rat" 1984, Cancer Res. 44:536-542.

International Search Report and Written Opinion for PCT/US2007/073578 dated Jul. 11, 2008.

International Search Report and Written Opinion for PCT/US2007/073580 dated Jul. 3, 2008.

International Search Report and Written Opinion for PCT/US2015/036618 dated Sep. 16, 2015.

Japan Office Action for JP2009520941 dated Sep. 18, 2012.

Koo et al. "Pharmacological Effects of Green Tea on the Gastrointestinal System" 2004, European Journal of Pharmacology 500:177-184.

Kountchev et al."Reduction of D-Dimer Levels After Therapeutic Administration of Antithrombin in Acquired Antithrombin Deficiency of Severe Sepsis" 2005, Critical Care 9:596-600.

Ma et al. "Creactive protein (CRP) rise is associated with the development of acute events in a model of plaque rupture and thrombosis" 2008, Life Science Journal 5(2): 21-24.

(56) References Cited

OTHER PUBLICATIONS

Ma et al. "Growth Inhibitory Effects of Quercetin on Bladder Cancer Cell" 2006, Frontiers of Bioscience 11:2275-2285.
Maclean et al."Dicumarol and Rutin in Retinal Vascular Disorders" 1947, American Journal of Ophthalmology 30:1093-1108.
Mahan et al. "New Antithrombotics: The Impact on Global Health Care" 2011, Thrombosis Research 127:518-524.
Marshall "Ambulatory Therapy for Thrombophlebitis with Rutin and Vitamin C" 1950, American Journal of Surgery 30:52-56.
Martin et al. "Role of Protein Disulfide Isomerase in Thrombus Formation in a Collagen-Induced Pathway of Thrombus Formation" 2010, Blood 116:156.
Matsui et al. "Snake venom proteases affecting hemostasis and thrombosis" Mar. 7, 2000, Biochim Biophys Acta. 1477(1-2):146-156.
Min et al. "The Chemistry and Medical Application of Tea Polyphenol" 2001, Hubei Chemical Industry 3:29-31 (Translation of English Abstract).
Nelson et al. "The Essential Medicinal Chemistry of Curcumin" Jan. 2017, J. Medicinal Chem. 60:1620-1637.
Oh et al. "Dual Roles of Quercetin in Platelets: Phosphoinositide-3-Kinase and MAP Kinases Inhibition, and cAMP-Dependent Vasodilator-Stimulated Phosphoprotein Stimulation" 2012, Evidence-Based Complementary and Alternative Medicine vol. 2012, Article ID 485262, 1-10.
Piergentili et al. "Bladder Cancer: Innovative Approaches Beyond the Diagnosis" May 2014, Current Medicinal Chemistry 21(20):2219-2236.
Raymond et al. "Sunitib Malate for the Treatment of Pancreatic Neuroendocrine Tumors" 2011, NEJM 364(6):501-513.
Sak "Site-Specific Anticancer Effects of Dietary Flavonoid Quercetin" Dec. 30, 2013, Nutrition and Cancer 66 (2):177-193.
Saucier et al. "Synergetic Activity of Catechin and Other Antioxidants" 1999, Journal of Agricultural and Food Chemistry 47(11):4491-4494.
Sekeroglu et al. "*Viscum Album* L. Extract and Quercetin Reduce Cyclophosphamide-induced Cardiotoxicity" 2011, Asian Pacific Journal of Cancer Prevention 12(11):2925-2931.
Sesink et al. "Quercetin Glucuronides but Not Glucosides Are Present in Human Plasma After Consumption of Quercetin-3-Glucoside or Quercetin-4-Glucoside" 2001, Human Nutrition and Metabolism Research Communication, pp. 1938-1941.
Shamay et al. "P-Selectin is a nanotherapeutic delivery target in the tumor microenvironment" Jun. 29, 2016, Sci. Transl. Med. 8(345):1-28.
Thomas et al. "Ascorbate and Phenolic Antioxidant Interations in Prevention of Liposomal Oxidation" 1992, Lipids 27(7).
Trout "Vitamin C and Cardiovascular Risk Factors.sup. 1-3" 1991, Am J Clin Nutr 53:322S-325S.
Walle et al. "Quercetin Glucosides Are Completely Hydrolyzed in Ileostomy Patients before Absorption" 2000, Human Nutrition and Metabolism Research Communication, pp. 2658-2661.
Wells et al. "Value of Assessment of Pretest Probability of Deep-Vein Thrombosis in Clinical Management" 1997, The Lancet 350:1795-1798.
Hamza et al. "Cancer-Associated Thrombosis: Risk Factors, Molecular Mechanisms, Future Management" Sep. 2020, Clinical and Applied Thrombosis/Hemostasis 26:1-13.

International Search Report and Written Opinion for PCT/US2022/037259 dated Oct. 19, 2022.
Mcdowell et al. "Anthropometric Reference Data for Children and Adults: United States, 2003-2006" Oct. 22, 2008, National Health Statistics Reports 10:1-48.
European Search Report and Written Opinion for EP21186637.1 dated Dec. 3, 2021.
Herrmann et al. "Homocystein und B-Vitamine im Fokusvon Gefaeß- und neurodegenerativen Erkrankungen" Jun. 2011, Ernaehrung und Medizin, Hippokrates Verlat ins MVS Medizinverlage Stuttgart GmbH & Co. KG 26:62-74.
International Search Report and Written Opinion for PCT/IB2022/054707 dated Aug. 24, 2022.
Malinow "Homocyst(e)ine, vitamins and genetic interactions in vascular disease" Apr. 1999, Canadian J. Cardiology 15 (supp B):31B-34B.
Rakel "Botanical supplements" 2007, Integrative Medicine 2nd Ed, Elsevier Saunders pp. 313-316.
Spittle et al. "The action of Vitamin C on Blood Vessels" Sep. 1974, American Heart Journal 88(3):387-388.
Indap et al. "Tumour Response to Quercetin, a Bioflavonoid with Some Promises in Therapies" 2006, Indian J. Pharma. Sci. 68:570-574.
Staedler et al. "Drug Combinations with Quercetin: Doxorubicin Plus Quercetin in Human Breast Cancer Cells" 2011 Cancer Chemotherapy Pharmacology 68:1161-1172.
Dai et al. "Effect of Quercetin on Coagulation Function in Model Mice with Acute Lymphoblastic Leukemia" Jun. 27, 2018, J. Emergency in Trad. Chinese Med. 27(6):970-973 (Chinese with full English translation).
European Supplemental Search Report and Written Opinion for EP 19891072.1 dated Jul. 8, 2022.
Kee et al. "Inhibitory Effect of Quercetin on Colorectal Lung Metastasis Through Inducing Apoptosis, and Suppression of Metastatic Ability" 2016, Phytomedicine 23:1680-1690.
Middleton et al. "The Effects of Plant Flavonoids on Mammalian Cells: Implications for Inflammation, Heart Disease and Cancer" 2000, Pharmacol. Rev.52(4):673-751.
Zwicker et al. "Targeting Protein Disulfide Isomerase With the Flavonoid Isoquercetin to Improve Hypercoagulability in Advanced Cancer" Feb. 21, 2019, JCI Insight 4(4):e125851.
Zwicker et al. "Targeting Protein Disulfide Isomerase with the Oral Flavonoid Isoquercetin Prevents Venous Thromboembolism in Advanced Cancer: Results of a Multi-Dose, Multi-Center, Phase II Clinical Trial (CATIQ Study)" Nov. 29, 2018, Blood 132(Supp 1):985 (abstract).
Invitation to Pay Additional Fees for PCT/IB2023/054726 dated Jul. 18, 2023.
Faes et al. "Red blood cells modulate structure and dynamics of venous clot formation in sickle cell disease" Jun. 6, 2019, Blood 133(23):2529-2541.
Kato "Sickle cells and sickle trait in thrombosis" 2019, Blood 133(3):2463.
Clinical Study NCT02195232 "Cancer Associated Thrombosis and Isoquercetin (CATIQ)" version 6 of Jan. 19, 2017, https://www.clinicaltrials.gov/study/NCT02195232?tab=history&a=6.

* cited by examiner

FIGURES 2A-B
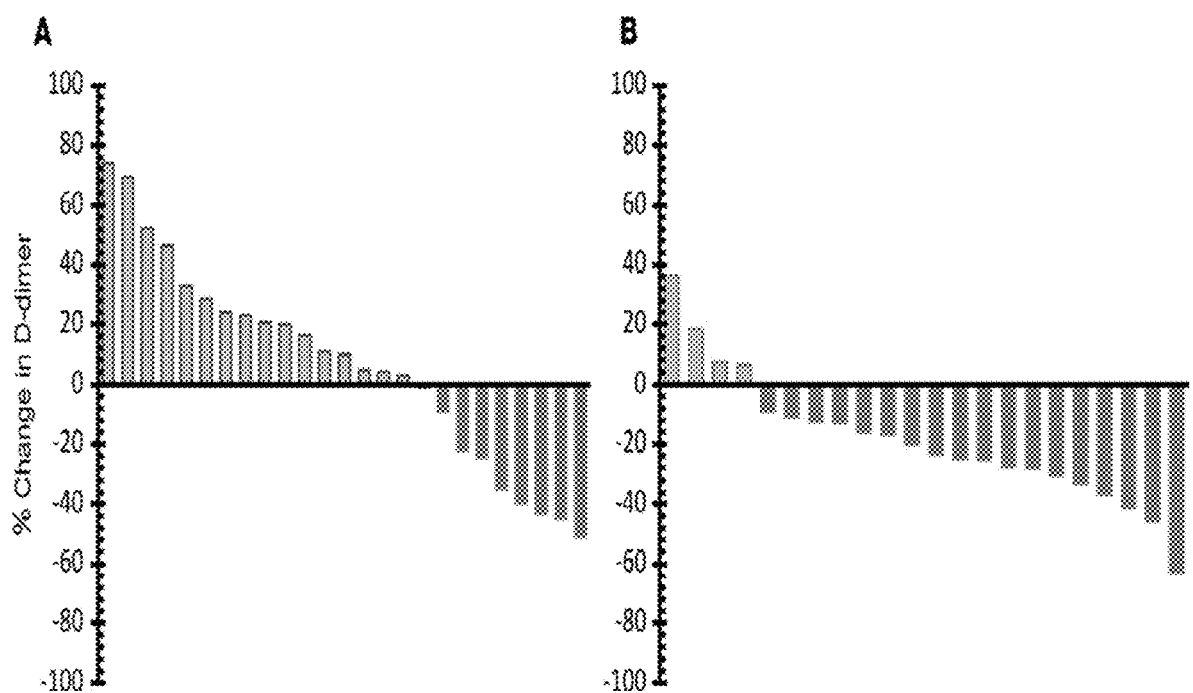

FIGURES 3A-D
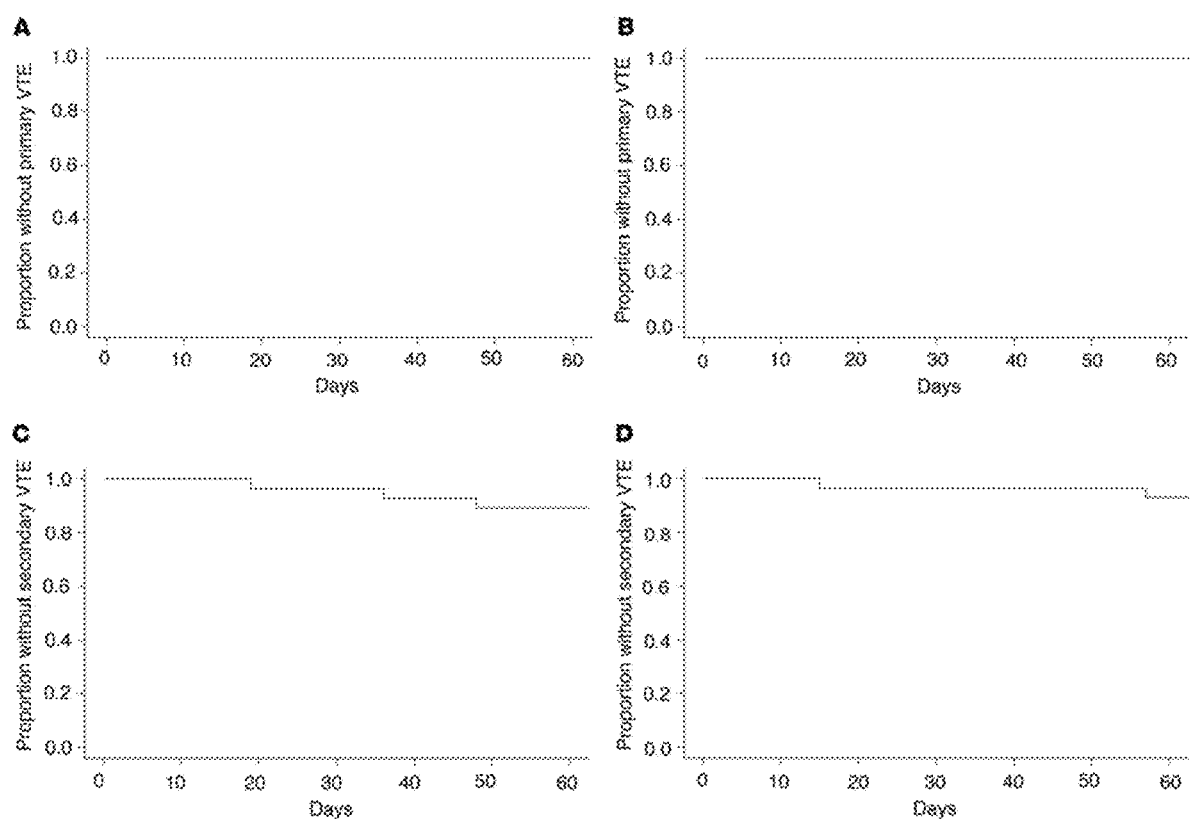

FIGURES 4A-B
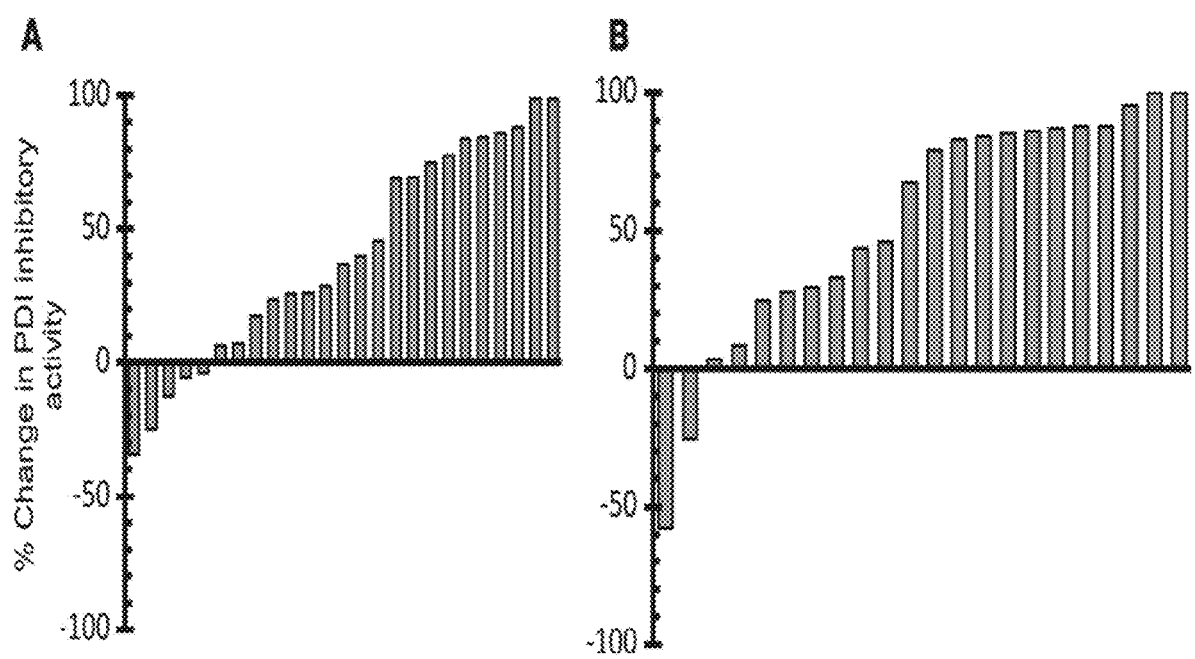

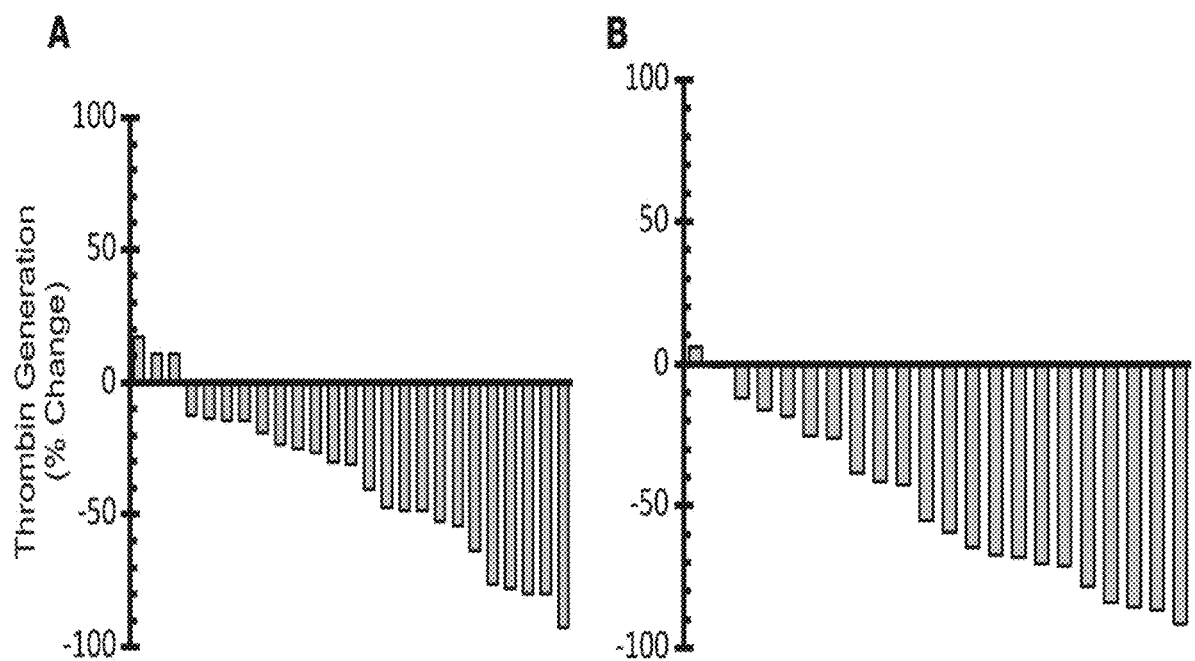
FIGURES 5A-B

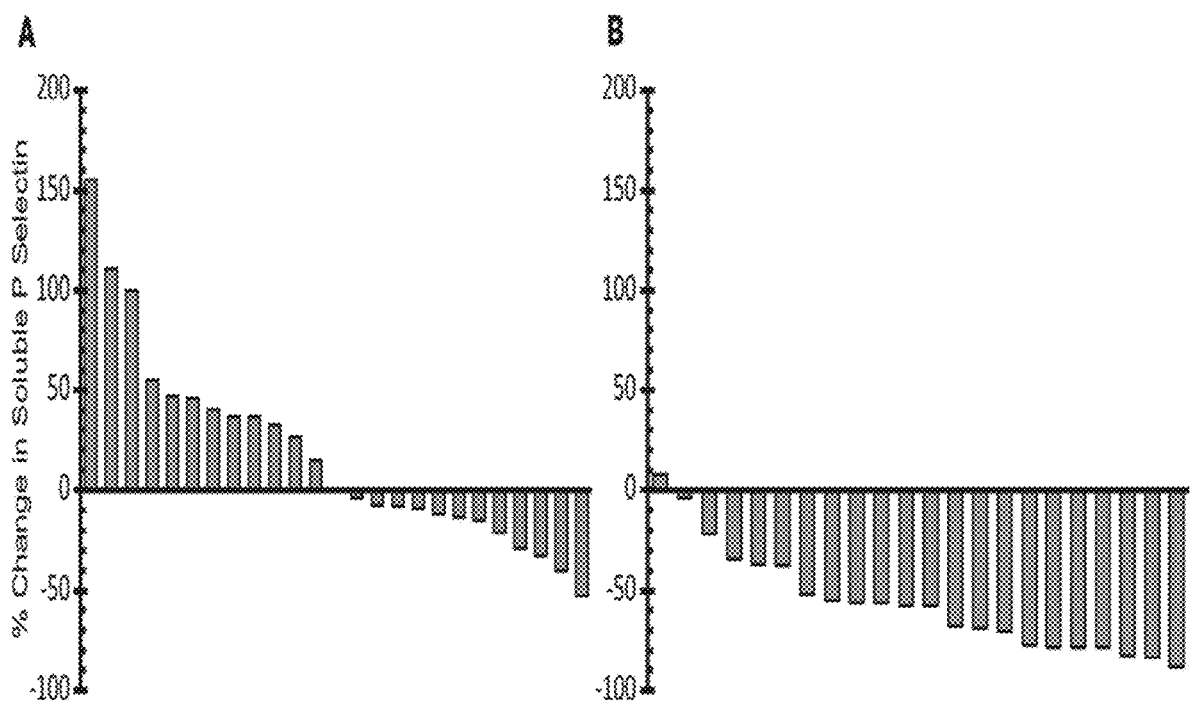
FIGURES 6A-B

COMPOSITIONS AND METHODS FOR REDUCING MAJOR THROMBOTIC EVENTS IN CANCER PATIENTS

CROSS-REFERENCE TO RELATED APPLICATIONS

This application claims priority to U.S. Provisional Application No. 62/773,696, filed Nov. 30, 2018, which is hereby incorporated by reference in its entirety.

GOVERNMENT INTEREST

This invention was made with government support under NIH grant number HL112302 awarded by National Institutes of Health. The government has certain rights in the invention.

SUMMARY OF THE INVENTION

The present invention relates to methods for reducing soluble P-selectin and major thrombotic events in cancer patients.

Various embodiments describe a method for reducing soluble P-selectin in a patient with cancer comprising administering to the patient an effective amount of isoquercetin or quercetin.

Some embodiments describe a method for reducing or preventing formation of a thrombus in a patient with cancer comprising administering to the patient an effective amount of isoquercetin or quercetin.

In some embodiments a method for promoting tumor regression in a patient with cancer comprising administering to the patient an effective amount of isoquercetin or quercetin is described.

Various embodiments describe a pharmaceutical composition for reducing soluble P-selectin in a patient with cancer comprising 500-1000 mg of isoquercetin or quercetin and a pharmaceutically acceptable excipient.

Some embodiments describe pharmaceutical composition for reducing or preventing formation of a thrombus in a patient with cancer comprising 500-1000 mg of isoquercetin or quercetin and a pharmaceutically acceptable excipient.

In some embodiments a pharmaceutical composition for promoting tumor regression in a patient with cancer comprising 500-1000 mg of isoquercetin or quercetin and a pharmaceutically acceptable excipient is described.

Some embodiments describe a pharmaceutical composition for stabilizing or reducing metastatic cancer in a patient with cancer comprising 500-1000 mg of isoquercetin or quercetin and a pharmaceutically acceptable excipient.

Various embodiments describe the oral dose of isoquercetin or quercetin is 500 mg per day. In further embodiments, the oral dose of isoquercetin or quercetin is 1000 mg per day.

In further embodiments, the soluble P-selectin is decreased at least about 30% when compared to a reference or baseline level of soluble P-selectin, following administration of the isoquercetin or quercetin.

In yet further embodiments, soluble P-selectin decrease ranges from 30-40%, 40-50%, 55-60%, 60-70%, 70-75%, or 75-80% when compared to a reference or baseline level of soluble P-selectin, following administration of the isoquercetin or quercetin.

In yet further embodiments, the patient has been diagnosed with metastatic cancer. In further embodiments, the metastatic cancer is colorectal cancer, pancreatic cancer, or non-small cell lung cancer.

In further embodiments, the metastatic cancer is selected from the group consisting of metastasizing forms of Hodgkin lymphoma, colorectal cancer, cervical cancer, lung cancer, skin cancer such as squamous cell cancer or basal cell carcinoma, head and neck cancer, gastric cancer, and pancreatic cancer.

In further embodiments, the cancer is selected from the group consisting of estrogen receptor-dependent breast cancer, estrogen receptor-independent breast cancer, hormone receptor-dependent prostate cancer, hormone receptor-independent prostate cancer, brain cancer, renal cancer, glioblastoma, colon cancer, familial adenomatous polyposis (FAP), colorectal cancer, pancreatic cancer, bladder cancer, esophageal cancer, stomach cancer, genitourinary cancer, gastrointestinal cancer, uterine cancer, ovarian cancer, astrocytomas, gliomas, skin cancer, squamous cell carcinoma, Keratoakantoma, Bowen disease, cutaneous T-Cell Lymphoma, melanoma, basal cell carcinoma, actinic keratosis; ichtiosis; acne, acne vulgaris, sarcomas, Kaposi's sarcoma, osteosarcoma, head and neck cancer, small cell lung carcinoma, non-small cell lung carcinoma, leukemia, lymphomas and/or other blood cell cancers.

In further embodiments, the patient exhibits no severe adverse events (grade 3 or 4 toxicities) during treatment.

In further embodiments, the patient exhibits no primary venous thromboembolism (VTE) during treatment. In yet further embodiments, the patient exhibits no VTE for at least 30-60 days following treatment.

In further embodiments, the patient exhibits no major hemorrhages during treatment.

In further embodiments, the patient exhibits a decrease in platelet-dependent thrombin generation of from about 30-60% when compared to a reference or baseline level of platelet dependent thrombin, following administration of the isoquercetin or quercetin.

In further embodiments, the patient exhibits decreased D-dimer plasma concentration of about 20-30% when compared to a reference or baseline level of D-dimer plasma concentration, following administration of the isoquercetin or rutin.

In further embodiments, the isoquercetin or quercetin is administered in a composition comprising about 20 micrograms to about 3 grams of Vitamin B3, and optionally further comprises about 200 micrograms to about 3 grams of Vitamin C, and further optionally comprises 1000 micrograms to about 3000 micrograms of folic acid.

In further embodiments, the patient exhibits an elevated level of soluble P-selectin prior to administration of isoquercetin or quercetin, when compared to a reference or baseline level of soluble P-selectin.

Various embodiments describe a pharmaceutical composition for reducing soluble P-selectin in a patient with cancer comprising 500-1000 mg of isoquercetin or quercetin and a pharmaceutically acceptable excipient.

Various embodiments describe a pharmaceutical composition for reducing or preventing formation of a thrombus in a patient with cancer comprising 500-1000 mg of isoquercetin or quercetin and a pharmaceutically acceptable excipient.

Various embodiments describe a pharmaceutical composition for promoting tumor regression in a patient with cancer comprising 500-1000 mg of isoquercetin or quercetin and a pharmaceutically acceptable excipient.

Various embodiments describe a pharmaceutical composition for stabilizing or reducing metastatic cancer in a patient with cancer comprising 500-1000 mg of isoquercetin or quercetin and a pharmaceutically acceptable excipient.

In additional embodiments, the composition further comprises about 20 micrograms to about 3 grams of Vitamin B3.

In additional embodiments, the composition further comprises about 200 micrograms to about 3 grams of Vitamin C.

In additional embodiments, the composition further comprises 1000 micrograms to about 3000 micrograms of folic acid.

In additional embodiments, the composition comprises 1000 mg of isoquercetin or quercetin.

BRIEF DESCRIPTION OF THE DRAWINGS

FIGS. 2A-B are waterfall plots of change in D-dimer following administration of isoquercetin. The waterfall plot data show baseline versus end-of-study comparisons of D-dimer values for each patient according to the dose of isoquercetin administered. FIG. 2A is a plot that illustrates the median change in D-dimer was +9.9% (Paired T-test 0.92) in Cohort A with 500 mg isoquercetin. FIG. 2B is a plot showing the median decrease in D-dimer was −21.9% in Cohort B with 1000 mg isoquercetin (P=0.0002).

FIGS. 3A-D are graphs illustrating the cumulative incidence of venous thromboembolism. Venous thromboembolisms (VTE) were monitored clinically and by lower extremity ultrasound at completion of the 2-month study. Shown is the proportion of patients remaining free of VTE through the course of the study. There were no primary VTE in either the 500-mg isoquercetin cohort (FIG. 3A) or the 1000-mg isoquercetin cohort (FIG. 3B). The cumulative incidence of all secondary VTE endpoints (i.e., superficial thrombosis and distal thrombosis) is shown for both the 500-mg cohort (FIG. 3C) and the 1000-mg cohort (FIG. 3D).

FIGS. 4A-B are plots showing the measurement of plasma PDI inhibitory activity following isoquercetin administration. The waterfall plots show baseline versus end-of-study comparisons for each patient. FIG. 4A shows the median change in PDI inhibitory activity was +37.0% (paired t test, P<0.001) with 500 mg isoquercetin. FIG. 4B shows the median change in PDI inhibitory activity was +73.3% with 1000 mg isoquercetin (P<0.001).

FIGS. 5A-B are plots showing the measurement of platelet-dependent thrombin generation activity following isoquercetin administration. The waterfall plots showing baseline and follow-up platelet-dependent thrombin generation following isoquercetin administration. Change (%) for each patient shown in a waterfall plot for 500 mg isoquercetin (FIG. 5A) and 1000 mg isoquercetin (FIG. 5B). The administration of isoquercetin resulted in a significant decrease in thrombin generation in both cohort A (median change −31.1%, P<0.001) and cohort B (median change −57.2%, P=0.004).

FIGS. 6A-B are plots showing the measurement of plasma P selectin levels following isoquercetin administration. The Waterfall plots show baseline and follow-up soluble P selectin values in plasma following isoquercetin administration. Change (%) for each patient shown in a waterfall plot for 500 mg isoquercetin (FIG. 6A) and 1000 mg isoquercetin (FIG. 6B).

DETAILED DESCRIPTION

Definitions

Figure 1:
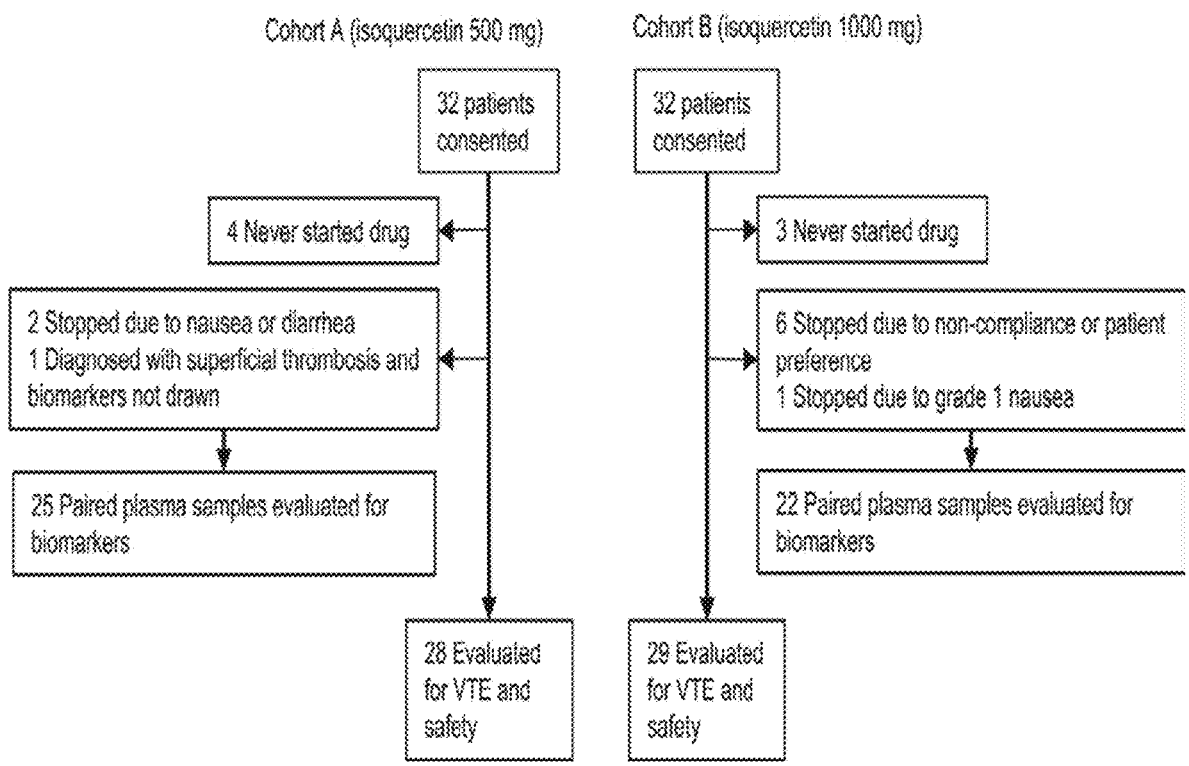
FIG. 1 is a flow diagram of patients enrolled in the clinical trial according to isoquercetin treatment allocation. The isoquercetin was administered in the clinical trial in a composition including the vitamin C and vitamin B3 as set out further herein.

Before the present compositions and methods are described, it is to be understood that this invention is not limited to the particular processes, formulations, compositions, or methodologies described, as these may vary. It is also to be understood that the terminology used in the description is for the purpose of describing the particular versions or embodiments only, and is not intended to limit the scope of embodiments herein which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of embodiments herein, the preferred methods, devices, and materials are now described. All publications mentioned herein are incorporated by reference in their entirety. Nothing herein is to be construed as an admission that embodiments herein is not entitled to antedate such disclosure by virtue of prior invention.

It must also be noted that as used herein and in the appended claims, the singular forms "a," "an," and "the" include plural reference unless the context clearly dictates otherwise.

As used herein, the term "about" means plus or minus 10% of the numerical value of the number with which it is being used. Therefore, about 50% means in the range of 45%-55%.

The term "subject" as used herein includes, but is not limited to, humans (also typically referred to as "patients") and non-human vertebrates such as wild, domestic, and farm animals. In certain embodiments, the subject described herein is an animal. In certain embodiments, the subject is a mammal. In certain embodiments, the subject is a human. In certain embodiments, the subject is a non-human animal. In certain embodiments, the subject is a non-human mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

The terms "treat," "treated," or "treating" as used herein refers to both therapeutic treatment and prophylactic or preventative measures, wherein the object is to inhibit, prevent or slow down or reduce the full effect or likelihood of (lessen) any undesired physiological condition, disorder or disease, or to improve, inhibit, or otherwise obtain beneficial or desired clinical results. For the purposes of this invention, beneficial or desired clinical results include, but are not limited to, improvement or alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

The term "inhibit" includes the administration of a compound according to embodiments described herein to prevent the onset of the symptoms, alleviating the symptoms, or eliminating the disease, condition or disorder.

By "pharmaceutically acceptable", it is meant the carrier, diluent or excipient must be compatible with the other ingredients of the topical formulation and not deleterious to the recipient thereof.

The term "blood thinning medication" refers to an antiplatelet drug, e.g., clopidogrel bisulfate, heparin, warfarin, enoxaparin, abciximab, eptifibatide, tirofiban, prasugrel, ticlopidine, beraprost, prostacyclin, iloprost, treprostinil, aspirin, aloxiprin, carbasalate calcium, indobufen, triflusal, dipyridamole, picotamide, terutroban, cilostazol, cloricromen, ditazole; or an anticoagulant, e.g., acenocoumarol, coumatetralyl, dicoumarol, ethyl biscoumacetate, phenprocoumon, clorindione, diphenadione, phenindione, tioclomarol, bemiparin, certoparin, dalteparin, nadroparin, parnaparin, reviparin, tinzaparin, fondaparinux, idraparinux, danaparoid, sulodexide, dermatan sulfate, apixaban, betrixaban, edoxaban, otamixaban, rivaroxaban, bivalirudin, lepirudin, desirudin, argatroban, dabigatran, melagatran, ximelagatran, regimen 1 (REG1; a combination of RB-006, a Factor IXa antagonist, and its oligonucleotide active control agent RB-007), defibrotide, ramatroban, antithrombin III, or drotrecogin alfa.

The term "thrombotic disorder" refers to many distinct conditions that cause or increase the risk of a venous or arterial thrombotic event, including but not limited to, atrial fibrillation, thrombosis due to a mechanical heart valve, myocardial infarction, unstable angina, deep vein thrombosis, acute ischemic stroke, pulmonary embolism, atherosclerosis, factor V Leiden, antithrombin III deficiency, protein C deficiency, protein S deficiency, prothrombin gene mutation (G20210A), hyperhomocysteinemi a, antiphospholipid antibody syndrome, anticardiolipin antibody, thrombosis syndrome, lupus anticoagulant syndrome, malignancy, major surgery, immobilization, oral contraceptive use, thalidomide use, especially in combination with dexamethasone, heparin-induced thrombocytopenia, pregnancy, myeloproliferative disorders, inflammatory bowel disease, nephrotic syndrome, paroxysmal nocturnal hemoglobinuria, hyperviscosity syndrome, Waldenstrom's macroglobulinemia, and trauma. The term "thrombotic disorder" also refers to thrombosis induced by cancer, e.g., multiple myeloma and other hematologic cancers, adenocarcinoma, cancer of the pancreas, stomach, ovaries, prostate, colon, lung, brain, breast, kidney, skin, cervix, and ear-nose-throat cancer.

"Vitamin $B_3$" mentioned herein includes vitamin $B_3$ in its various forms, including niacinamide, nicotinic acid, nicotinamide, inositol hexaniacinate.

"Vitamin C" mentioned herein includes vitamin C (i.e., L-ascorbic acid, D-ascorbic acid, or both) and its salts (e.g., sodium ascorbate).

"Folic acid" mentioned herein includes vitamin $B_9$, folate, pteroylglutamic acid, and L-methyl folate.

The term "improve" is used to convey that the compounds or methods of embodiments herein change either the appearance, form, characteristics and/or the physical attributes of the condition or tissue to which it is being provided, applied or administered.

The terms "improving," "treating," and "reducing" refer to the administration of an effective amount of an isoquercetin, quercetin or rutin composition of the invention to a subject, who needs to improve one or more of the above-mentioned conditions or has one or more of the just-mentioned disorders, or a symptom or a predisposition of one of more of the disorders or conditions, with the purpose to improve one or more of these conditions, or to prevent, cure, alleviate, relieve, remedy, or ameliorate one or more of these disorders, or the symptoms or the predispositions of one or more of them. The term "administration" covers oral or parenteral delivery to a subject the quercetin, isoquercetin, or rutin composition (or any suitable derivative thereof) of the invention in any suitable form, e.g., food product, beverage, tablet, capsule, suspension, and sterile injectable solution. The term "parenteral" refers to subcutaneous, intracutaneous, intravenous, intramuscular, intraarticular, intraarterial, intrasynovial, intrasternal, intrathecal, intralesional, and intracranial injection, as well as various infusion techniques. An "effective amount" refers to a dose of the isoquercetin, quercetin, or rutin composition that is sufficient to provide a therapeutic benefit (e.g., reducing the levels of PDI activity in the serum and/or soluble P selectin in the patient in need thereof, e.g. a cancer patient with elevated levels of soluble P selectin). In certain embodiments, an effective amount of isoquercetin is about 1000 mg. In certain embodiments, the effective amount of isoquercetin can range from about 1,000 mg-2,000 mg. In additional embodiments an effective amount of isoquercetin ranges from about 2,000 mg-2,500 mg. A particularly preferred effective amount of isoquercetin is 1000 mg.

Methods of Treatment

Thrombus formation involves several sequential steps that typically begin following a skin laceration or a vascular injury. Circulating platelets first adhere to the site of injured endothelial cells and a series of events occurs that allows activation of these platelets. Activated platelets then recruit additional platelets to the site of injury, where they aggregate to form a plug until a stable clot forms. Inactive coagulation factors, which are always present and circulating in the bloodstream, are then sequentially activated in a process known as the coagulation cascade. The coagulation cascade ultimately leads to a stable fibrin-containing clot.

Thrombotic disorders are a group of inherited and acquired disorders that cause abnormal activation of the hemostatic system, leading to an increased risk of venous and arterial thrombosis. Cancer is among the acquired disorders that greatly increase the risk of thrombosis. Tumor cells, by expressing high levels of tissue factor on their surface, cause a hypercoagulable state. Tissue factor is required for initiating the just-mentioned coagulation cascade.

Among the factors involved in thrombus formation is protein disulfide isomerase (PDI). PDI is secreted by activated endothelial cells and platelets, after which it plays a critical role in thrombus formation. PDI can activate tissue factor, which leads to activation of the coagulation cascade, ultimately resulting in fibrin deposition and thrombus formation.

Protein disulfide isomerase is a thiol isomerase that is primarily localized to the endoplasmic reticulum where it serves an essential role in protein folding. However, PDI can also be released from cells in disease states or following tissue injury and contribute to pathological processes. PDI has been implicated in cancer, neurodegenerative disease, infectious disease, and thromboembolism. In the context of thromboembolic disease, PDI is released from activated platelets and endothelial cells and is postulated to modulate through oxidation, reduction, or isomerization a number of extracellular coagulation substrates as factor XI, tissue factor, factor V, vitronectin, $\alpha IIb\beta 3$, and $\alpha V\beta 3$. Targeting PDI activity with blocking antibodies or small molecules prevents both platelet accumulation and fibrin generation at the site of vascular injury in several distinct animal models of thrombosis.

Additional methods and compositions for preventing and reducing venous or arterial thrombotic events are needed.

Some embodiments of the present invention describe a method for reducing soluble P-selectin in a patient with cancer comprising administering to the patient an effective amount of an isoquercetin, or derivative compound, or quercetin or a quercetin derivative compound, or a rutin or rutin derivative compound, according to any embodiment described herein. In some embodiments soluble P-selectin is decreased at least about 30% when compared to a reference or baseline level of soluble P-selectin following administration of an isoquercetin, or derivative compound, or a quercetin or quercetin derivative compound. In some embodiments soluble P-selectin decrease ranges from 30-40%, 40-50%, 55-60%, 60-70%, 70-75%, or 75-80% when compared to a reference or baseline level of soluble P-selectin following administration of an isoquercetin, or derivative compound, or a quercetin or quercetin derivative compound.

Some embodiments of the present invention describe a method for reducing or preventing formation of a thrombus in a patient with cancer comprising administering to the patient an effective amount of an isoquercetin, or derivative compound, or quercetin or a quercetin derivative compound, or a rutin or rutin derivative compound, according to any embodiment described herein.

Some embodiments of the present invention describe a method for promoting tumor regression in a patient with cancer comprising administering to the patient an effective amount an isoquercetin, or derivative compound, or quercetin or a quercetin derivative compound, or a rutin or rutin derivative compound, according to any embodiment described herein.

Some embodiments of the present invention describe a method for stabilizing or reducing metastatic cancer in a patient with cancer comprising administering to the patient an effective amount of an isoquercetin, or derivative compound, or quercetin or a quercetin derivative compound, or a rutin or rutin derivative compound, according to any embodiment described herein.

Some embodiments of the present invention describe a method for reducing soluble P-selectin in a patient with cancer comprising administering to the patient an effective amount of an isoquercetin, or derivative compound, or quercetin or a quercetin derivative compound, or a rutin or rutin derivative compound, according to any embodiment described herein.

Some embodiments of the present invention describe a method for reducing or preventing formation of a thrombus in a patient with cancer comprising administering to the patient an effective amount of an isoquercetin, or derivative compound, or quercetin or a quercetin derivative compound, or a rutin or rutin derivative compound, according to any embodiment described herein.

Some embodiments of the present invention describe a method for promoting tumor regression in a patient with cancer comprising administering to the patient an effective amount of an isoquercetin, or derivative compound, or quercetin or a quercetin derivative compound, or a rutin or rutin derivative compound, according to any embodiment described herein.

Some embodiments of the present invention describe a method for stabilizing or reducing metastatic cancer in a patient with cancer comprising administering to the patient an effective amount of an isoquercetin, or derivative compound, or quercetin or a quercetin derivative compound, or a rutin or rutin derivative compound, according to any embodiment described herein.

In some embodiments, according to any method described herein, the patient exhibits no severe adverse events (grade 3 or 4 toxicities) during treatment.

In some embodiments, according to any method described herein, the patient exhibits no primary venous thromboembolism (VTE) during treatment.

In some embodiments, according to any method described herein, the patient exhibits no VTE for at least 30-60 days following treatment.

In some embodiments, according to any method described herein, the patient exhibits no major hemorrhages during treatment.

In some embodiments, according to any method described herein, the patient exhibits a decrease in platelet-dependent thrombin generation of from about 30-60% when compared to a reference or baseline level of platelet dependent thrombin following administration of the quercetin or quercetin derivative.

In some embodiments, according to any method described herein, the patient exhibits decreased D-dimer plasma concentration of about 20-30% when compared to a reference or baseline level of D-dimer following administration of the quercetin or quercetin derivative.

Rutin, Quercetin, Isoquercetin and Related Derivatives

The terms "isoquercetin" "quercetin" and "rutin" refer to certain active compounds for administration as described herein.

Isoquercetin (2-(3,4-Dihydroxyphenyl)-5,7-dihydroxy-3-[(2S,3R,4S,5S,6R)-3,4,5-trihydroxy-6-(hydroxymethyl)oxan-2-yl]oxychromen-4-one) is a 3-O-glucoside of quercetin having the following structure:

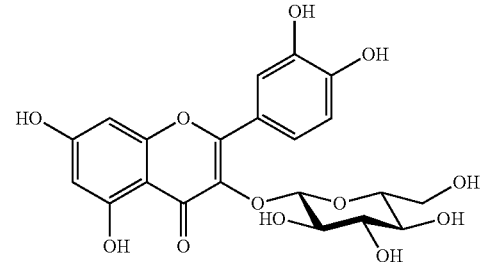

Rutin (2-(3,4-dihydroxyphenyl)-5,7-dihydroxy-3-[α-L-rhamnopyranosyl-(1→6)-β-D-glucopyranosyloxy]-4H-chromen-4-one) is another common glycoside that has disaccharide rutinose (α-L-rhamopyranosyl-(1→6-β-D-glucopyranose) attached at the 3 O position of the quercetin having the following structure:

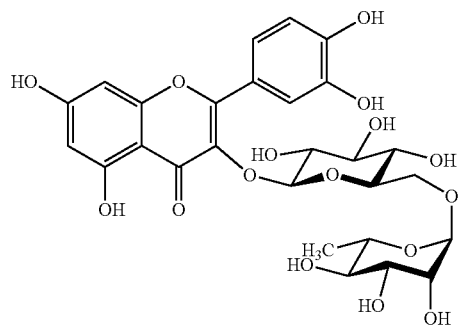

Quercetin is characterized by the following structure:

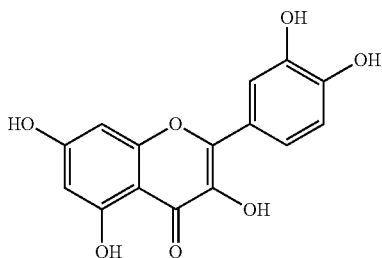 [SMILES: O=c1c(O)c(-c2ccc(O)c(O)c2)oc2cc(O)cc(O)c12]

In embodiments described herein, the active compound may encompass quercetin or quercetin derivatives such as: quercetin-5-O-glucoside, quercetin-7-O-glucoside, quercetin-9-O-glucoside, quercetin-3 O-[.alpha.-rhamnosyl-(1.fwdarw.2)-.alpha.-rhamnosyl-(1.fwdarw.-.6)]-.beta.-glucoside, quercetin-3-O-galactoside, quercetin-7-O-galactoside, quercetin-3-O-rhamnoside, isoquercetin, rutin, and quercetin-7-O-galactoside. After digestion, quercetin derivatives are converted in the body to quercetin aglycon and/or other active derivatives, including methylated, sulphated and gluconorated forms which are absorbed in the body.

In some embodiments described herein the compounds for use in the present methods are isoquercetin or quercetin. In some embodiments the compound is isoquercetin. In some embodiments the compound is rutin. Suitable conjugates or derivatives include methylates, sulfates and glucoronides.

While not wishing to be bound by theory, it is believed that isoquercetin and rutin, as single active agents inhibit the enzyme activity of protein disulfide isomerase (PDI). As described herein, PDI and soluble P selectin also both plays a role in the initiation of the coagulation/thrombotic cascade. By lowering the level of soluble P selectin in a patient, and in particular in a cancer patient who exhibits elevated soluble P selectin levels, it is believed that isoquercetin, quercetin, or rutin can inhibit or prevent thrombus formation in a patient, and in particular in a patient with cancer. Additionally, the antithrombotic activity of isoquercetin or rutin can be evaluated in humans by measuring D-dimer levels in plasma samples from patients treated with isoquercetin or rutin. D-dimer, a small protein fragment present in the blood, is a fibrin degradation product. The level of D-dimer in the blood increases after a thrombotic event due to its release from blood clots via fibrinolysis.

In any embodiment described herein, the quercetin or quercetin derivative can be added to the composition either in a pure form or as an ingredient in a mixture (e.g., a plant extract). Examples of commercially available quercetin include QU995 (containing 99.5% quercetin) and QU985 (containing 98.5% quercetin) from Quercegen Pharmaceuticals LLC (Boston, Mass.).

Examples of commercially available isoquercetin compounds include those available from Quercegen Pharmaceuticals LLC: ISQ 995 AN (99.5% pure all-natural isoquercetin) and ISQ 995 CIT (99.5% pure isoquercitrin). Additional methods and isoquercetin compositions can be found in U.S. Pat. Nos. 7,745,486 and 7,745,487, incorporated herein by reference.

Cancers

As used herein, the types of cancer can be selected from the group consisting of estrogen receptor-dependent breast cancer, estrogen receptor-independent breast cancer, hormone receptor-dependent prostate cancer, hormone receptor-independent prostate cancer, brain cancer, renal cancer, glioblastoma, colon cancer, familial adenomatous polyposis (FAP), colorectal cancer, pancreatic cancer, bladder cancer, esophageal cancer, stomach cancer, genitourinary cancer, gastrointestinal cancer, uterine cancer, ovarian cancer, astrocytomas, gliomas, skin cancer, squamous cell carcinoma, Keratoakantoma, Bowen disease, cutaneous T-Cell Lymphoma, melanoma, basal cell carcinoma, actinic keratosis; ichtiosis; acne, acne vulgaris, sarcomas, Kaposi's sarcoma, osteosarcoma, head and neck cancer, small cell lung carcinoma, non-small cell lung carcinoma, leukemia, lymphomas and/or other blood cell cancers.

Additional cancers that will benefit from the methods described herein include cancers associated with certain viruses (and include improving a pre-cancerous condition during viral infection). Such conditions include those associated with Human T-cell leukemia virus type, also called human T-lymphotrophic virus (HTLV-1) which is linked to adult T-cell leukemia/lymphoma. Another such cancer include those associated with human papillomavirus (HPV), which has at least 12 strains that can cause cancer in men and women, including anal, cervical, penile, throat, vaginal and vulvar cancer. Additional condition includes those associated with human herpes virus 8 (HHV-8), which is associated with Kaposi sarcoma in people who have a weakened immune system (e.g. patients with HIV). Similarly, there are numerous cancers associated with HIV, which is believed to damage the immune system and reduce defenses against other oncoviruses. HIV-associated cancers include Kaposi sarcoma, non-Hodgkin's and Hodgkin's lymphoma, cervical cancer, and cancers of the anus, liver, mouth and throat and lung. Additionally, hepatitis C is a leading cause of liver cancer, and can cause non-Hodgkin's lymphoma, and as such can benefit from the methods described herein. Similarly, hepatitis B is a leading cause of liver cancer, and these conditions can benefit from the methods described herein. Finally, Epstein-Barr virus (EBV) infection increases the risk of Burkitt lymphoma, some types of Hodgkin's and non-Hodgkin's lymphoma and stomach cancer, and these conditions can also benefit from the methods described herein.

In certain embodiments, the cancer is a metastasizing cancer. A "metastasizing cancer" is a cancer which may form or often forms metastases. A metastasizing cancer which has already spread from the part of the body where it started, i.e. the primary site, to other parts of the body, is also denoted metastatic cancer. When cancer cells break away from a tumor, they can travel to other areas of the body through the bloodstream or the lymph system. Such cancer cells may then form new tumors in other areas of the body.

In certain embodiments, the cancer is a metastasizing cancer selected from the group consisting of metastasizing forms of Hodgkin lymphoma, colorectal cancer, cervical cancer, lung cancer, skin cancer such as squamous cell cancer or basal cell carcinoma, head and neck cancer, gastric cancer, pancreatic cancer, head and neck squamous cell cancer, and breast cancer.

In some embodiments the metastatic cancer is colorectal cancer, pancreatic cancer, or non-small cell lung cancer.

In certain embodiments, the cancer is classifiable as Stage III or Stage IV according to the TNM anatomic/prognostic group system of the cancer staging system of the American Joint Committee on Cancer. In additional embodiments, the cancer is classifiable as Stage IV according to the TNM anatomic/prognostic group system of the cancer staging system of the American Joint Committee on Cancer.

In certain embodiments, the cancer is a metastasizing cancer selected from the group consisting of metastasizing forms of Hodgkin lymphoma, colorectal cancer, cervical cancer, lung cancer, skin cancer such as squamous cell cancer or basal cell carcinoma, head and neck cancer, gastric cancer, pancreatic cancer, and breast cancer, wherein said metastasizing cancer is classifiable as Stage IV according to the TNM anatomic/prognostic group system of the cancer staging system of the American Joint Committee on Cancer (7.sup.th edition, 2010, Springer).

In certain embodiments, the isoquercetin, quercetin, or rutin compositions are used for treating cancers or reducing PDI and/or soluble P-selectin in subjects with metastases that have already formed, such as metastasizing forms of Hodgkin lymphoma, colorectal cancer, cervical cancer, head and neck cancer, gastric cancer, non-small cell lung cancer, pancreatic cancer and breast cancer in a mammalian, typically human subject. In additional embodiments, the isoquercetin, quercetin, or rutin compositions are used for treating cancers or reducing plasma PDI and/or soluble P-selectin in subjects without metastatic cancer, but who exhibit cancer only at a primary site. Additionally, it is expected that the methods and treatments described herein will be effective in treating any solid or blood cell cancer, since all patients with these cancers, whether or not they are metastatic, will benefit from reduced levels of plasma PDI and/or soluble P-selectin, and furthermore will benefit from the elimination of venous thromboembolisms (VTE's) without increasing the risk of major hemorrhage. It is noted that patients with cancer typically exhibit high levels of soluble P selectin, and as a result, are at an elevated risk for developing venous thromboembolisms (VTE's) and related thrombotic conditions.

It is believed that administering isoquercetin, as shown in the results described herein, will benefit all cancer patients and serve to "delay progression" promote a state of "non-progression" or remission in these patients, in part by reducing their soluble P-selectin levels. This is due at least in part because, P-selectin has a functional role in metastasis of tumors similar to E-selectin. P-selectin is expressed on the surface of both stimulated endothelial cell and activated platelet and helps cancer cells invade into the bloodstream for metastasis. Moreover, it has been known that platelet facilitates tumor metastasis by forming complexes with tumor cells and leukocytes in the vasculature thus preventing recognition by macrophage, this is thought to contribute to the seeding of tumor microemboli to distant organs. In vivo mice experiments have shown that reduction in circulating platelets could reduce cancer metastasis.

Additionally, one of the sulfated ligands is chondroitin sulfate, a type of glycosaminoglycan (GAG). Its activity in tumor metastasis has been probed by the addition of heparin that functions to blocks tumor metastasis. In addition to GAGs, mucin is of interest in P-selectin mediated tumor metastasis. Selective removal of mucin results in reduced interaction between P-selectin and platelets in vivo and in vitro.

Likewise, heparin has long been known to represent anti-heparanase activity that is to keep an endoglycosidase from degrading heparin sulfate, one of the glycosaminoglycans, and to effectively inhibit P-selectin. Despite a striking effect of heparin on tumor progression shown in a number of clinical trials, the use of heparin as anti-cancer agent is limited because of its risk, which might induce adverse bleeding complications. Thus, the selective reduction of soluble P-selectin by isoquercetin, without risks of major thrombotic events, is a major advance that will provide therapeutic benefits to all cancer patients, potentially serving as a long-term "metastasis reduction factor" that will provide periods of progression-free survival and durable remission.

The isoquercetin, quercetin, or rutin compositions, or any derivative thereof, according to any embodiment described herein may be administered by oral or parenteral (e.g., intramuscular, intraperitoneal, intravenous, ICV, intracisternal injection or infusion, subcutaneous injection, or implant) dosage form and may be formulated, alone or together, in suitable dosage unit formulations containing conventional non-toxic pharmaceutically acceptable carriers, adjuvants and vehicles appropriate for each route of administration. The compounds and compositions described herein may also be formulated as a controlled-release formulation.

The isoquercetin, quercetin, or rutin compositions, or any derivative thereof, according to any embodiment described herein can be administered in a wide range of dosage-forms including, for example, solid dosage forms and liquid dosage forms. Solid dosage forms may include powders, tablets, pills, capsules, suppositories, or dispersible granules. A solid carrier can be one or more substances that function as a diluting agent, flavor additive, solvent, lubricant, suspension agent, binder, preservative, tablet-disintegrating substance or encapsulating material. In powdered form, the carrier may be a finely pulverized solid including lactose, hydroxypropylmethylcellulose and PVP, mixed with an appropriate amount of the active ingredient. Appropriate carriers for powder and tablet forms include for example magnesium carbonate, magnesium stearate, talc, sugar, lactose, pectin, dextrin, stiffeners, gelatins, tragacanth, methylcellulose, and sodium carboxymethylcellulose.

Liquid dosage forms include for example solutions, suspensions, and emulsions. Also included are compositions in solid form that are meant to be converted to liquid form shortly prior to consumption. These forms may include, in addition to the active ingredients, artificial colors, flavors, stabilizers, buffers, natural or artificial sweeteners, dispersing agents, thickeners, dissolving agents and the like.

Solutions or mixtures may be administered directly to the nasal cavity using conventional means, such as drops or sprays. The composition may be produced in individual or multi-dose forms. Multi-dose forms would include a dropper, pipette or atomizer that delivers a predetermined volume of the composition.

The isoquercetin, quercetin, or rutin compositions, or any derivative thereof, according to any embodiment described herein may be provided in individual dosage units that contain a suitable amount of the active ingredient.

The individual doses may be provided in a package, or as a kit that includes a measuring device, e.g., a device for measuring oral or injectable dosages (i.e., a measuring cup, needle, or syringe). The kit can also include, other materials such buffers, diluents, filters, and package inserts with instructions for use. A label may be present on the on the kit to indicate that the composition is used for a specific therapy, and may also indicate directions for use.

If desired, the compositions of the present invention may further comprise one or more additional active agents. Where it is appropriate, any of the active agents may be administered in the form of the compound per se, and/or in the form of a salt, polymorph, ester, amide, prodrug, derivative, or the like, provided the salt, polymorph, ester, amide, prodrug or derivative is suitable pharmacologically. Where it is appropriate, salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For any active agents that may exist in enantiomeric forms, the active agent may be incorporated into the present compositions either as the racemate or in enantiomerically enriched form.

In some embodiments the dosage of the isoquercetin, quercetin, or rutin compositions, or any derivative thereof, according to any embodiment described being administered will depend on the condition being treated, the particular compound, and other clinical factors such as age, sex, weight, and health of the subject being treated, the route of administration of the compound(s), and the type of composition being administered (tablet, gel cap, capsule, solution, suspension, inhaler, aerosol, elixir, lozenge, injection, patch, ointment, cream, etc.). It is to be understood that the present disclosure has application for both human and animal use. The amount of the quercetin or quercetin derivative according to any embodiment described, required for use in treatment will be ultimately at the discretion of the attendant physician or clinician.

In some embodiments, the isoquercetin, quercetin, or rutin compositions, or any suitable derivative thereof, can be in a soft chew composition that includes isoquercetin, quercetin, or rutin or any suitable derivative thereof, niacinamide, ascorbic acid, sodium ascorbate, folic acid, sugar, corn syrup, sucralose, soy lecithin, sunflower lecithin, corn starch, glycerin, palm oil, xylitol, carrageenan, FD&C Yellow #6, FD&C Yellow #5, or natural or artificial flavors. Optionally, any of the quercetin, quercetin derivative, isoquercetin, isoquercetin derivative, or rutin or rutin derivative compositions described herein can further comprise components such as vitamin $B_3$, vitamin C and or folic acid. An exemplary soft chew composition (5.15 g) includes 250 mg of isoquercetin, 12.9 mg of vitamin $B_3$ (i.e., niacinamide), and 382.8 mg of vitamin C (i.e., L-ascorbic acid and sodium ascorbate). In further exemplary embodiments, the components of the exemplary soft chew are the same, except the active agent is replaced with 500 mg or 1000 mg of isoquercetin. For example, a subject can take one to eight servings (e.g., 4 servings) of this soft chew composition daily. The amounts taken can vary depending on, for example, the disorder or condition to be treated and the physical states of the subject. Another exemplary composition of this soft chew includes 5.25 wt % of quercetin, 0.25 wt % of vitamin $B_3$, and 7.81 wt % of vitamin C (i.e., L-ascorbic acid and sodium ascorbate) plus 200 µg of folic acid per chew.

In some embodiments the isoquercetin, quercetin, or rutin is administered in a composition comprising Vitamin B3, and optionally further comprises Vitamin C, and further optionally comprises folic acid.

In some embodiments the isoquercetin, quercetin, or rutin is administered in a composition comprising about 20 micrograms to about 3 grams of Vitamin B3, and optionally further comprises about 200 micrograms to about 3 grams of Vitamin C, and further optionally comprises 1000 micrograms to about 3000 micrograms of folic acid (e.g. folate).

When the above-described composition is in powder form, it can be used conveniently to prepare beverage, paste, jelly, capsules, or tablets. Lactose and corn starch are commonly used as diluents for capsules and as carriers for tablets. Lubricating agents, such as magnesium stearate, are typically included in tablets.

The oral bioavailability of isoquercetin, quercetin, or rutin in the above-mentioned capsule or tablet formulations can be improved by the use of certain additives. For example, a capsule or tablet can include acid treated gelatin, citrate, potassium hydroxide, and/or a cyclodextrin. A preferred amount of these additives per mg of isoquercetin, quercetin, or rutin is 0.01-0.5 mg potassium hydroxide, 0.01-0.7 mg acid treated gelatin, 0.1-1 mg citrate, and 0.01-1 mg of a cyclodextrin. Isoquercetin, quercetin, or rutin, in the presence of the additives, can have a solubility in an aqueous solution of 2-5%. Additionally, the pH of a isoquercetin, quercetin, or rutin-containing formulation with improved oral bioavailability can be between pH 7 and pH 12.

The isoquercetin, quercetin, or rutin composition administered in the methods of this invention can be a dietary supplement or a pharmaceutical formulation. As a dietary supplement, additional nutrients, such as minerals or amino acids may be included. A pharmaceutical formulation can be a sterile injectable or infusible solution that contains the isoquercetin, quercetin, or rutin composition together with pharmaceutically acceptable excipients. The isoquercetin, quercetin, or rutin composition can also be a food product. As used herein, the term "food" broadly refers to any kinds of liquid and solid/semi-solid materials that are used for nourishing humans and animals, for sustaining normal or accelerated growth, or for maintaining stamina or alertness. Examples of human food products include, but are not limited to, tea-based beverages, juice, coffee, milk, jelly, cookies, cereals, chocolates, snack bars, herbal extracts, dairy products (e.g., ice cream, and yogurt), soy bean product (e.g., tofu), and rice products.

The dosage of the compound as an active ingredient in the compositions of this invention may be varied so that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize.

In some embodiments, the therapeutically effective amount will be about 500 mg to up to 5 grams daily. In certain additional embodiments, the therapeutically effective amount will be about 4 grams, or 3 grams, or even 2 grams. In certain embodiments, the therapeutically effective amount will be about 500 mg to about 2000 mg daily.

In some embodiments the therapeutically effective amount is between a lower limit of about 500 mg/day, about 525 mg/day, about 550 mg/day, about 575 mg/day, about 600 mg/day, about 625 mg/day, about 650 mg/day, about 675 mg/day, about 700 mg/day, about 725 mg/day, about 750 mg/day, about 775 mg/day, about 800 mg/day, about 825 mg/day, about 850 mg/day, about 875 mg/day, about 900 mg/day, about 925 mg/day, about 950 mg/day, about 975 mg/day, about 1000 mg/day, about 1025 mg/day, about 1050 mg/day, about 1075 mg/day, about 1100 mg/day, 1125 mg/day, about 1150 mg/day, about 1175 mg/day, about 1200 mg/day, 1225 mg/day, about 1250 mg/day, about 1275 mg/day, about 1300 mg/day, 1325 mg/day, about 1350 mg/day, about 1375 mg/day, about 1400 mg/day, 1425 mg/day, about 1450 mg/day, about 1475 mg/day, about 1500 mg/day, about 1525 mg/day, about 1550 mg/day, about 1575 mg/day, about 1600 mg/day, about 1625 mg/day, about 1650 mg/day, about 1675 mg/day, about 1700 mg/day, about 1725 mg/day, about 1750 mg/day, about 1775 mg/day, about 1800 mg/day, about 1825 mg/day, about 1850 mg/day, about 1875 mg/day, about 1900 mg/day, about 1925 mg/day, about 1950 mg/day, about 1975 mg/day, about 2000 mg/day, about 2025 mg/day, about 2050 mg/day, about 2075 mg/day, about 2100 mg/day, 2125 mg/day, about 2150 mg/day, about 2175 mg/day, about 2200 mg/day, 2225 mg/day, about 2250 mg/day, about 2275 mg/day, about 2300 mg/day, 2325 mg/day, about 2350 mg/day, about 2375 mg/day, about 2400 mg/day, 2425 mg/day, about 2450 mg/day, about 2475 mg/day, about 2500 mg/day, about 2525 mg/day, about 2550 mg/day, about 2575 mg/day, about 2600 mg/day, about 2625 mg/day, about 2650 mg/day, about 2675 mg/day, about 2700 mg/day, about 2725 mg/day, about 2750 mg/day, about 2775 mg/day, about 2800 mg/day, about 2825 mg/day, about 2850 mg/day, about 2875 mg/day, about 2900 mg/day, about 2925 mg/day, about 2950 mg/day, about 2975 mg/day, about 3000 mg/day, about 3025 mg/day, about 3050 mg/day, about 3075 mg/day, about 3100 mg/day, 3125 mg/day, about 3150 mg/day, about 3175 mg/day, about 3200 mg/day, 3225 mg/day, about 3250 mg/day, about 3275 mg/day, about 3300 mg/day, 3325 mg/day, about 3350 mg/day, about 3375 mg/day, about 3400 mg/day, 3425 mg/day, about 3450 mg/day, about 3475 mg/day, about 3500 mg/day, about 3525 mg/day, about 3550 mg/day, about 3575 mg/day, about 3600 mg/day, about 3625 mg/day, about 3650 mg/day, about 3675 mg/day, about 3700 mg/day, about 3725 mg/day, about 3750 mg/day, about 3775 mg/day, about 3800 mg/day, about 3825 mg/day, about 3850 mg/day, about 3875 mg/day, about 3900 mg/day, about 3925 mg/day, about 3950 mg/day, about 3975 mg/day, about 4000 mg/day, about 4025 mg/day, about 4050 mg/day, about 4075 mg/day, about 4100 mg/day, 4125 mg/day, about 4150 mg/day, about 4175 mg/day, about 4200 mg/day, 4225 mg/day, about 4250 mg/day, about 4275 mg/day, about 4300 mg/day, 4325 mg/day, about 4350 mg/day, about 4375 mg/day, about 4400 mg/day, 4425 mg/day, about 4450 mg/day, about 4475 mg/day, about 4500 mg/day, about 4525 mg/day, about 4550 mg/day, about 4575 mg/day, about 4600 mg/day, about 4625 mg/day, about 4650 mg/day, about 4675 mg/day, about 4700 mg/day, about 4725 mg/day, about 4750 mg/day, about 4775 mg/day, about 4800 mg/day, about 4825 mg/day, about 4850 mg/day, about 4875 mg/day, about 4900 mg/day, about 4925 mg/day, about 4950 mg/day, about 4975 mg/day, and about 5000 mg/day; and an upper limit of about 5000 mg/day, about 4975 mg/day, about 4950 mg/day, about 4925 mg/day, about 4900 mg/day, about 4875 mg/day, about 4850 mg/day, about 4825 mg/day, about 4800 mg/day, about 4775 mg/day, about 4750 mg/day, about 4725 mg/day, about 4700 mg/day, about 4675 mg/day, about 4650 mg/day, about 4625 mg/day, about 4600 mg/day, about 4575 mg/day, about 4550 mg/day, about 4525 mg/day, about 4500 mg/day, 4475 mg/day, about 4450 mg/day, about 4425 mg/day, about 4400 mg/day, about 4375 mg/day, about 4350 mg/day, about 4325 mg/day, about 4300 mg/day, about 4275 mg/day, about 4250 mg/day, about 4225 mg/day, about 4200 mg/day, about 4175 mg/day, about 4150 mg/day, about 4125 mg/day, about 4100 mg/day, about 4075 mg/day, about 4050 mg/day, about 4025 mg/day, about 4000 mg/day, 3975 mg/day, about 3950 mg/day, about 3925 mg/day, about 3900 mg/day, about 3875 mg/day, about 3850 mg/day, about 3825 mg/day, about 3800 mg/day, about 3775 mg/day, about 3750 mg/day, about 3725 mg/day, about 3700 mg/day, about 3675 mg/day, about 3650 mg/day, about 3625 mg/day, about 3600 mg/day, about 3575 mg/day, about 3550 mg/day, about 3525 mg/day, about 3500 mg/day, 3475 mg/day, about 3450 mg/day, about 3425 mg/day, about 3400 mg/day, about 3375 mg/day, about 3350 mg/day, about 3325 mg/day, about 3300 mg/day, about 3275 mg/day, about 3250 mg/day, about 3225 mg/day, about 3200 mg/day, about 3175 mg/day, about 3150 mg/day, about 3125 mg/day, about 3100 mg/day, about 3075 mg/day, about 3050 mg/day, about 3025 mg/day, about 3000 mg/day, 2975 mg/day, about 2950 mg/day, about 2925 mg/day, about 2900 mg/day, about 2875 mg/day, about 2850 mg/day, about 2825 mg/day, about 2800 mg/day, about 2775 mg/day, about 2750 mg/day, about 2725 mg/day, about 2700 mg/day, about 2675 mg/day, about 2650 mg/day, about 2625 mg/day, about 2600 mg/day, about 2575 mg/day, about 2550 mg/day, about 2525 mg/day, about 2500 mg/day, 2475 mg/day, about 2450 mg/day, about 2425 mg/day, about 2400 mg/day, about 2375 mg/day, about 2350 mg/day, about 2325 mg/day, about 2300 mg/day, about 2275 mg/day, about 2250 mg/day, about 2225 mg/day, about 2200 mg/day, about 2175 mg/day, about 2150 mg/day, about 2125 mg/day, about 2100 mg/day, about 2075 mg/day, about 2050 mg/day, about 2025 mg/day, about 2000 mg/day, 1975 mg/day, about 1950 mg/day, about 1925 mg/day, about 1900 mg/day, about 1875 mg/day, about 1850 mg/day, about 1825 mg/day, about 1800 mg/day, about 1775 mg/day, about 1750 mg/day, about 1725 mg/day, about 1700 mg/day, about 1675 mg/day, about 1650 mg/day, about 1625 mg/day, about 1600 mg/day, about 1575 mg/day, about 1550 mg/day, about 1525 mg/day, about 1500 mg/day, 1475 mg/day, about 1450 mg/day, about 1425 mg/day, about 1400 mg/day, about 1375 mg/day, about 1350 mg/day, about 1325 mg/day, about 1300 mg/day, about 1275 mg/day, about 1250 mg/day, about 1225 mg/day, about 1200 mg/day, about 1175 mg/day, about 1150 mg/day, about 1125 mg/day, about 1100 mg/day, about 1075 mg/day, about 1050 mg/day, about 1025 mg/day, about 1000 mg/day, about 975 mg/day, about 950 mg/day, about 925 mg/day, about 900 mg/day, about 875 mg/day, about 850 mg/day, about 825 mg/day, about 800 mg/day, about 775 mg/day, about 750 mg/day, about 725 mg/day, about 700 mg/day, about 675 mg/day, about 650 mg/day, about 625 mg/day, about 600 mg/day, about 575 mg/day, about 550 mg/day, about 525 mg/day, and about 500 mg/day The compounds may be administered on a regimen of 1 to 4 times per day, such as once, twice, three times or four times per day.

The efficacy of administering isoquercetin to reduce the hypercoagulability in cancer patients was evaluated. Venous thromboembolism (VTE) is commonly observed in cancer patients and is a leading cause of mortality in this population. In high risk cancer patients especially where protocol-driven radiographic monitoring for deep vein thrombosis is implemented, the incidence of VTE within initial few months of chemotherapy commonly exceeds 20%. Cancer patients are also at an increased risk of bleeding which has limited the adoption of routine primary thromboprophylaxis in cancer outpatients receiving chemotherapy. Developing antithrombotics that reduce the incidence of VTE without increasing the risk of major hemorrhage would broadly impact the care of patients with advanced malignancy, as well as any patient with cancer.

EXAMPLES

Example 1

Multi-Center, Multi-Dose Phase II Trial

A multi-center, multi-dose phase II trial was conducted to evaluate, among other markers and readouts, the efficacy of targeting protein disulfide isomerase (PDI) along with soluble P-selectin with isoquercetin to reduce the hypercoagulability in cancer patients at high risk for venous thromboembolism (VTE). Patients received isoquercetin at 500 mg (cohort A) or 1000 mg (cohort B) daily for 56 days with laboratory assays at the beginning and at completion of study (along with duplex ultrasound). The primary endpoint was a reduction in D-dimer and the primary clinical endpoint included pulmonary embolism or proximal deep vein thrombosis, and also included measuring the level of soluble P-selectin. (See, Zwicker et al., *JCI Insight.* 2019; 4(4): e125851.)

A total of 64 patients were consented for participation on the study. All patients who received at least 1 dose of isoquercetin were evaluated for the development of VTE, hemorrhage and safety (FIG. 1). There were a total of 28 evaluable patients in Cohort A (isoquercetin 500 mg daily) and 29 in Cohort B (isoquercetin 1000 mg daily). Table 1 shows baseline demographic data for the two dosing cohorts. The groups were similarly distributed for the pancreatic, non-small lung, and colorectal malignancies. Approximately half of the patients were enrolled at the start of the initial chemotherapeutic regimen and half at the start of second line therapy.

D-Dimer and PDI Inhibition

The primary endpoint of the study was comparison of plasma D-dimer at baseline and end-of-study. D-dimer is liberated from cross-linked fibrin following plasma-mediated degradation. D-dimer is the most validated and commonly utilized laboratory assay in the clinic to detect deep vein thrombosis. In patients with advanced cancer, plasma D-dimer levels are commonly elevated and correlate with an increased risk for developing of VTE.

As shown in FIG. 2A, in cohort A, a nonsignificant median change in D-dimer of +9.90% was observed following the administration of isoquercetin 500 mg daily in the 25 paired samples available (paired t-test P=0.92). In cohort B, FIG. 2B, D-dimer was reduced in the majority of individuals (18 of 22) with a significant median change of −21.9% (paired t-test P=0.0002).

PDI inhibitory activity can be monitored using a plasma-based assay that measures the dequenching of eosin moieties within a di-eosin-GSSG fluorescent probe. In both cohorts, the PDI inhibitory activity significantly decreased following 2 months of daily isoquercetin administration (FIGS. 4A-B). The median change in PDI inhibitory activity for Cohort A (FIG. 4A) was +37.0% (P=0.001) and +73.3% in Cohort B (FIG. 4B) (P<0.001).

Venous Thromboembolism

Patients were monitored for the development of venous thromboembolism (VTE) throughout the two months of the study including an end-of-study bilateral lower extremity ultrasound to evaluate for asymptomatic lower extremity proximal DVT. Shown in FIGS. 3A-D is the proportion of patients remaining free of VTE through the course of the study. There were no VTE that met criteria for the primary VTE endpoint in either cohort (FIGS. 3A-B). There were three secondary VTE endpoints recorded in cohort A (FIG. 3C, two incidental catheter-associated DVT diagnosed with re-staging imaging and one lower extremity superficial venous clot). In cohort B (FIG. 3D), there were two secondary endpoint thrombotic events recorded (superficial venous clot of the lower extremity and incidental thrombosis observed in a lingular pulmonary vein on re-staging imaging).

Inhibition of Thrombin Generation

The platelet-dependent thrombin generation assay measures thrombin generation following platelet activation and requires PDI. As shown in FIGS. 5A-B, the administration of isoquercetin resulted in a significant decrease in thrombin generation in both cohort A (FIG. 5A) (median change −31.1% P=0.001) and cohort B (FIG. 5B) (median change −57.2%, P=0.004). Correlation between PDI inhibitory activity in plasma and platelet-dependent thrombin generation confirmed the PDI-dependency of thrombin generation (Spearman coefficient 0.29, P=0.004). There was significant correlation between increased plasma PDI inhibitory activity and decreased thrombin generation (Pearson correlation coefficient 0.45, P=0.002)

In standard coagulation assays following administration of isoquercetin, there were no effects detected. In cohort A, the mean PT at baseline was 14.0 seconds compared with 14.3 seconds at 2-months (P=0.37) and mean PTT was 49.6 seconds at baseline and 45.6 seconds at study completion (P=0.11). In cohort B, the mean PT at baseline was 15.1 seconds compared with 15.2 seconds at 2-months (P=0.88) and mean PTT was 54.2 seconds and 51.9 seconds, at respective time points (P=0.37).

P-selectin is a transmembrane adhesion receptor that is externalized from α-granules in platelets and Weibel-Palade bodies in endothelial cells following cell activation. P-selectin can be shed from the cell surface following externalization and P-selectin shedding is increased in cardiovascular disease, sepsis, and cancer. Increased levels of soluble P-selectin have been shown to be predictive of VTE in cancer cohorts. As PDI inhibition alters platelet and endothelial reactivity, baseline versus end-of-treatment plasma levels of soluble P-selectin following treatment with isoquercetin was compared. As shown in FIGS. 6A-B, there was no change in soluble P-selectin in Cohort A (FIG. 6A) (median change −0.3%, P=0.26). In contrast, in Cohort B (FIG. 6B) soluble P-selectin decreased in all patients except one, with a median decrease of −57.9% (P<0.001). Five patients in each cohort concomitantly took low-dose aspirin, but the administration of low-dose aspirin did not influence the observed change in soluble P selectin in cohort A (P=0.62) or cohort B (P=0.81).

Safety

There were no major hemorrhages observed in either treatment cohort in modified intention-to treat analyses. One patient in Cohort A developed grade 1 epistaxis and two patients in Cohort B developed non-severe gastrointestinal bleeding (grades 1 hemorrhoid and grade 2 rectal bleeding attributed to radiation proctitis). The most commonly reported toxicities on study were nausea and diarrhea which are common toxicities of the concurrent chemotherapeutics administered. There were no severe adverse events (grade 3 or 4) that were attributed to the administration of isoquercetin. There were no deaths reported following the initiation of isoquercetin during the 2 months of follow-up.

The results of this phase II clinical trial validate extracellular PDI as a viable therapeutic target for antithrombotic therapy. At 1000 mg daily, isoquercetin inhibited plasma PDI activity and significantly reduced plasma D-dimer levels. In a cancer population considered higher risk for thrombosis and hemorrhage, none of the following were observed in the treated patients: proximal deep vein thrombosis, pulmonary emboli, or major hemorrhage.

Elevations of plasma D-dimer are associated with an increased risk of thrombosis in cancer patients. Therapeutic anticoagulation with direct oral anticoagulants reduces D-dimer by approximately 20% which is similar to the percentage decrease observed at the 1000 mg dosing of isoquercetin in healthy subjects (Clinicaltrials.gov NCT01722669). The lower dose of isoquercetin (500 mg) did not reduce D-dimer levels. Prior pharmacokinetic studies suggest that plasma concentrations of isoquercetin at 500 mg fall below the inhibitory concentration (IC50) of PDI activity in vitro.

Thus, the data illustrating reduction in soluble P selectin levels associated with the cohort B 1000 mg dose indicates that P selectin is a good target and perhaps indicator of reduced likelihood and reduced risk of thrombosis in cancer patients. In a cancer population considered higher risk for thrombosis and hemorrhage, none of the following were observed in the treated patients: proximal deep vein thrombosis, pulmonary emboli, or major hemorrhage.

The observed 37% reduction in PDI inhibitory activity at 500 mg daily may be below the threshold needed to affect plasma levels of D-dimer. The decision to proceed with a clinical trial at both dose levels was based on absence of longitudinal safety data with isoquercetin especially in a patient population considered at increased risk for hemorrhage (per advisement of the Food and Drug Administration). This decision was also in part based on uncertainty regarding the cumulative effects of repeated dosing on PDI activity and the poorly understood mechanisms whereby PDI regulates thrombosis, especially considering that the dose of quercetin-3-rutinoside required to inhibit platelet aggregation in vitro is orders of magnitude higher than that needed to inhibit platelet aggregation in vivo. Interestingly, despite not observing a reduction in D-dimer at the lower dose level of isoquercetin (Cohort A at 500 mg), significant reductions in platelet-dependent thrombin generation were measured and no primary VTE endpoints were recorded. These data indicate that D-dimer may not be a sensitive biomarker to predict the therapeutic efficacy of isoquercetin to prevent VTE, and in fact the reduction of soluble P selectin may be a suitable biomarker.

The absence of VTE in both of the cohorts is an intriguing and important observation. Similar to another phase II study performed to evaluate the efficacy of low molecular weight heparin to prevent thrombosis in high risk patients, an aggressive screening strategy was implemented to identify asymptomatic proximal deep vein thrombi. The same inclusion and exclusion criteria was utilized as a prior trial addressing pharmacokinetic and pharmacodynamic safety measures in healthy subjects (Clinicaltrials.gov NCT01722669) where VTE was documented in approximately 20% of those who did not receive pharmacologic thromboprophylaxis (*JCI Insight* 2017; 2(1)e89373). In other cancer studies that implemented protocol-mandated imaging for VTE, over 20% of high-risk patients are diagnosed with VTE. A pre-specified VTE independent adjudication committee was utilized in the present clinical trial and included a central radiology review of all radiographic studies indicative of a thrombotic event. Confirmation of a reduction in the incidence of proximal DVT or pulmonary emboli (PE) with isoquercetin will require further clinical evaluation, such as a large randomized-controlled clinical trial.

At the doses evaluated in the current trial, isoquercetin administration reduced platelet-dependent thrombin generation assay but did not cause serious bleeding. Complete inhibition of PDI activity in plasma with blocking antibodies has been shown to prolong tail bleeding times in mice. Kim and colleagues observed that tail bleeding times were not prolonged in platelet-specific PDI-deficient mice despite an overall decrease in the size of a thrombus following a laser-induced injury (Kim K. et al. *Blood.* 2013; 122(6): 1052-61). In view of these data and observations, it is believed that hemostatic-antithrombotic balance is similar to that observed in animal models whereby incomplete inhibition of extracellular PDI activity alters the propagation of a thrombus without significantly impacting hemostasis.

These results showing that isoquercetin significantly lowers soluble P-selectin levels is an activity not shared by other standard anticoagulants such as warfarin, dabigatran, or rivaroxaban. P-selectin mediates binding to the glycoprotein ligand-1 on the surface of leukocytes to promote the generation of tissue factor bearing microparticles and thrombus formation. Soluble P-selectin is formed by proteolytic cleavage of the ectodomain following leukocyte adhesion with activated platelets. Increased levels of soluble P-selectin are predictive of VTE in cancer patients. In a prospective study of 687 cancer patients, soluble P-selectin in the highest quartile was associated with a 2.6-fold greater risk of developing VTE compared with lower levels. Similarly, in a mouse model of cancer associated thrombosis, inhibition of P-selectin completely abrogated thrombus accumulation following infusion of pancreatic cancer cell-derived microparticles. These data suggest that P-selectin-mediated thrombosis plays a central role in the hypercoagulability of cancer and further supports the clinical development of isoquercetin specifically for the indication of cancer associated thrombosis.

In summary, cancer patients treated in cohorts A and B exhibited numerous therapeutic benefits from treatment with 500 mg or 1000 mg of isoquercetin over the course of 56 days. Similar benefits would be expected for treatment courses of any length, including 60 days, 90 days, 120 days, 150 days, 6 months, and for as long as treatment with isoquercetin is efficacious.

Importantly, there were no primary VTE endpoints observed in either cohort. For the primary D-dimer endpoint, the administration of isoquercetin 1000 mg decreased D-dimer plasma concentrations by a median of 21.9% (P=0.0002). In cohorts A and B an increase in median PDI inhibitory activity was measured in plasma at day 56 (37.0%, P=0.001; 73.3%, P<0.001, respectively). Corroborating the antithrombotic efficacy, a significant decrease in platelet-dependent thrombin generation was also observed (cohort A median decrease −31.1%, P=0.001; cohort B median decrease −57.2%, P=0.004) and circulating soluble P-selectin at the 1000 mg isoquercetin dose (median decrease −57.9%, P<0.001). There were no major hemorrhages observed.

The present clinical trial results show direct correlations between PDI activity and platelet-dependent thrombin generation, as well as PDI activity and D-dimer levels which point to the antithrombotic activity of isoquercetin being predominated by PDI inhibition. No grade 3 or 4 toxicities were reported that were attributed isoquercetin administration. These results are from the first clinical trial (Clinicaltrials.gov NCT02195232) to specifically evaluate the clinical efficacy of PDI inhibition in humans. The results illustrating that the administration of isoquercetin to cancer patients with metastatic disease successfully achieved all primary and secondary endpoints without a safety signal provides a critical validation step in the development of this class of therapeutics. Finally, these data suggest that P selectin-mediated thrombosis plays a central role in the hypercoagulability of cancer and further support the clinical development of isoquercetin for the indication of cancer-associated thrombosis.

METHODS

Study Design and Participants

TABLE 1

Baseline Demographics.
Total numbers in each cohort and percentages (in parenthesis).

|  | Cohort A n = 28 | Cohort B n = 29 |
|---|---|---|
| Sex | | |
| Female | 14 (50) | 9 (31) |
| Male | 14 (50) | 20 (69) |
| Age - median (range) | 65 (55-70) | 65 (58-69) |
| Disease type | | |
| Colorectal - Stage IV | 8 (29) | 11 (38) |
| NSCLC - Stage III | 1 (4) | 3 (10) |
| NSCLC - Stage IV | 8 (29) | 6 (21) |
| Pancreas - locally advanced | 9 (32) | 5 (17) |
| Pancreas - metastatic | 2 (7) | 4 (14) |
| Prior chemotherapy regimens | | |
| 0 | 16 (57) | 15 (52) |
| 1 | 12 (43) | 14 (48) |

CATIQ was an investigator-initiated, multi-center, multi-dose, open-label phase II clinical trial conducted at 10 sites in the United States. Eligible patients were required to have advanced cancer (unresectable or metastatic adenocarcinoma of the pancreas, stage IV colorectal cancer, or stage III/IV non-small lung cancer). Patients were enrolled within 4 weeks of initiating first or second-line chemotherapy. Additional inclusion criteria were: age≥18 years, life expectancy>4 months, Eastern Cooperative Oncology Group (ECOG) performance status≤2, absolute neutrophil count≥1×$10^9$/L, platelet count≥90×$10^9$/L, prothrombin time and partial thromboplastin time≤1.5-times greater than the institutional upper limit of normal, total bilirubin≤2.0 mg/dL, aspartate aminotransferase and alanine aminotransferase≤2.5 times the institutional upper limit of normal and creatinine≤2.0 mg/dL. Participants were excluded if they were receiving any other anticoagulant therapy, had known brain metastases, had a prior history of VTE within the last two years, had a history of hemorrhage requiring transfusion or hospitalization within the last two years, had concurrent use of anti-platelet agents (beyond aspirin 81 mg daily), or had evidence of disseminated intravascular coagulation. Patients were enrolled from oncology outpatient clinics between 2014 and 2018. All patients voluntarily gave written informed consent prior to initiation of study procedures. The protocol was approved by the institutional review boards of the 10 participating medical centers and centrally by the Dana Farber/Harvard Cancer Center. The protocol was additionally reviewed and approved by the Scientific Advisory Board of Quercegen Pharmaceuticals LLC. Study coordination and monitoring were performed by the Office of Human Research Studies and Office of Data Quality at Dana Farber/Harvard Cancer Center as well as Cancer Clinical Trials Office at Beth Israel Deaconess Medical Center.

Participants were sequentially enrolled into two dosing cohorts: Cohort A (isoquercetin 500 mg) and Cohort B (isoquercetin 1000 mg). Isoquercetin was supplied in capsules containing 250 mg of isoquercetin each with 10 mg added as overage to guarantee a minimum of 250 mg of isoquercetin per capsule with added Vitamin C and Vitamin $B_3$ by Quercegen Pharmaceuticals LLC (Boston, MA). The drug product capsules were manufactured by Pharmavize NV, Kleinmoer 4, 9030 Mariakerke, Belgium.

The ratio of components in the capsules was: 1:0.25:0.02 of isoquercetin, vitamin C, and vitamin $B_3$, respectively. It is noted that folic acid can optionally be present in the isoquercetin composition. Isoquercetin was taken orally daily for a total of 56 days. The first 5 patients of each cohort were monitored for evidence of toxicity prior (≥1 grade 3 or higher toxicity possibly related to isoquercetin) prior to the subsequent enrollment of 25 patients into each cohort. Patients were monitored for development of a venous thromboembolic event throughout the study including a bilateral lower extremity duplex ultrasound at end of study visit (day 56±5). Participants were taken off study if they developed an intercurrent illness that prevented further administration; unacceptable adverse events; poor compliance; participant preference; VTE or condition requiring therapeutic anticoagulation; requirement for prophylactic anticoagulation for >7 consecutive days; or grade≥3 hemorrhage or otherwise met the ISTH criteria for major hemorrhage. Doses were held for grade 2 hemorrhage or platelet count<50×$10^9$/L.

Outcome Measurement

Blood was drawn by peripheral venipuncture into 3.2% citrate. Plasma was separated at 2100 g for 20 minutes within one hour of specimen collection. A second centrifugation was performed at 2100 g for 20 minutes to generate platelet-free plasma and stored in aliquots at −80° C. until analysis. The primary endpoint of the study was a decrease in plasma D-dimer at end of study. D-dimer was measured centrally using Asserrachrom D-Di ELISA, considered the reference standard assay for D-dimer (Stago, France) (Meyer G. et al., *Blood Coagulation & Fibrinolysis.* 1998; 9(7):603-8.).

The primary VTE endpoint included any symptomatic proximal or distal deep vein thrombosis, symptomatic PE or fatal PE diagnosed by autopsy, asymptomatic proximal DVT diagnosed by protocol-specified ultrasound at end of study. All suspected VTE were assessed by an independent adjudication committee that included central radiologic review of images. Criteria for new VTE included any of the following: A) A new noncompressibility of lower extremity deep venous segments by compression ultrasound (distal lower extremity thrombus qualified for primary VTE endpoint only if symptomatic). B) Intraluminal defects in two or more views on pulmonary angiography, sudden contrast cut-off of one or more vessels greater than 2.5 mm in diameter on a pulmonary angiogram; a high probability VQ lung scan showing one or more segmental perfusion defects with corresponding normal ventilation (mismatch defect); or abnormal spiral CT showing thrombus in pulmonary vessels (subsegmental or larger). All other venous or arterial events were recorded and analyzed as secondary endpoints. Criteria for major hemorrhage was according to ISTH definition (Schulman S, and Kearon C. *J Thromb Haemost.* 2005; 3(4):692-4). All toxicities were graded according NCI Common Terminology Criteria for Adverse Events (CTCAE). Study oversight was performed by an independent Data Safety Monitoring Committee at Dana Farber Harvard Cancer Center.

PDI inhibition assay in plasma was performed as previously described (Stopa J.D. et al. *JCI insight.* 2017; 2(1): e89373). Human recombinant PDI dual-tagged with FLAG and streptavidin-binding peptide was expressed and isolated from *E. coli* (BL21) by affinity chromatography with streptavidin-linked agarose resin. Purified recombinant PDI was added at varying concentrations to filtered GSSG-treated plasma with 5 µM DTT and 150 nM di-eosin-GSSG. Enzymatic activity was monitored through the fluorescence of eosin (EGSH).

Di-eosin-GSSG Assay. Preparation of di-eosin-GSSG was performed as described. The platelet-poor plasma was filtered through a Millipore 30-kDa cutoff filter at 14,000 g and the filtrate incubated with 10 µM GSSG for 20 minutes at room temperature. Human recombinant PDI dual tagged with FLAG and streptavidin-binding peptide was expressed and isolated from E. coli (BL21) by affinity chromatography with streptavidin-linked agarose resin. Purified recombinant PDI was added at varying concentrations (0, 50, 100, and 250 nM) to filtered GSSG-treated plasma with 5 µM DTT and 150 nM di-eosin-GSSG. Enzymatic activity was monitored through the fluorescence of eosin (EGSH), which was excited at 525 nm and emission was recorded at 545 nm. Linear rates were obtained and converted to units of enzymatic activity per ml of PDI stock. Once standardized, 2 U/ml PDI was added to 5 µM DTT and 150 nM di-eosin-GSSG in a total volume of 80 µl with GSSG-treated filtered plasma. Percentage inhibition was assessed by the difference in measured units of activity from those of the standard. For the $IC_{50}$ determination, 100 µM recombinant PDI was incubated in GSSG-treated filtered plasma for 5 minutes with concentrations of quercetin analog ranging from 20 nM to 3 mM in GSSG-treated filtered plasma and then assayed for enzymatic activity as described. Percentage inhibition was normalized to the no-addition control (100%).

Platelet-dependent thrombin generation was performed according to previously published methodology (Stopa J D et al., JCI insight. 2017; 2(1):e89373; Jurk K et al. J Thromb Haemost. 2011; 9(11):2278-90). Briefly, platelet-free plasma was mixed with donor platelet-rich plasma diluted to a platelet concentration of 250,000 platelets per microliter in the presence of 5 mM GPRP and 6 mM $CaCl_2$, and then stimulated with 0.1 U/ml of thrombin. Samples were incubated for 90 min at room temperature with rotation, and thrombin levels were measured using cleavage of a fluorescent thrombin-specific substrate (Haemtech SN-20 Boc-L-FPR-ANSNH-C2H5) by excitation at 352 nm and emission as a function of time at 470 nm. Rates of substrate cleavage were used to calculate the concentration of thrombin in each sample.

Measurement of soluble P-selectin (CD62) was performed centrally using a commercial ELISA (Invitrogen/ThermoFisher Scientific #BMS219-4) and prothrombin time and partial thromboplastin time according to standard manufacturer protocol on a Sago Start 4 instrument (STA-Neoplastine CI Plus 5 #00606, STA-PTT Automate 5 #00595).

Statistical Analysis

Plasma D-dimer levels decrease approximately 20% following the initiation of therapeutic anticoagulation. The median baseline D-dimer measurement in a similarly designed study was 815 µg/L (Zwicker et al. Br J Haematol. 2013; 160(4):530-7). Based on an estimated standard deviation of 0.3 for the ratio of D-dimer at study completion compared to day 1, the target enrollment was 26 patients in each arm for 90% power to declare the reduction significant if true concentration at end of treatment was reduced by 20% (one-sided α=0.05).

The cumulative incidence of VTE or hemorrhage was assessed by competing risk analyses in order to account for death as a competing risk (Campigotto et al. J Thromb Haemost. 2012; 10(7):1449-51). Comparisons between baseline and follow-up measurements were performed using a two-tailed, paired T-test analyses. Comparison of baseline demographics were performed using Fisher's exact test. Statistical correlation between PDI inhibitory activity and D-dimer was assessed using a Pearson's correlation coefficient. Statistical significance was defined as P value<0.05.

General Methods

Standard methods in molecular biology are described Sambrook, Fritsch and Maniatis (1982 & 1989 $2^{nd}$ Edition, 2001 $3^{rd}$ Edition) Molecular Cloning, A Laboratory Manual, Cold Spring Harbor Laboratory Press, Cold Spring Harbor, NY; Sambrook and Russell (2001) Molecular Cloning, $3^{rd}$ ed., Cold Spring Harbor Laboratory Press, Cold Spring Harbor, NY; Wu (1993) Recombinant DNA, Vol. 217, Academic Press, San Diego, CA). Standard methods also appear in Ausbel, et al. (2001) Current Protocols in Molecular Biology, Vols. 1-4, John Wiley and Sons, Inc. New York, NY, which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) Current Protocols in Protein Science, Vol. 1, John Wiley and Sons, Inc., New York). Chemical analysis, chemical modification, post-translational modification, production of fusion proteins, glycosylation of proteins are described (see, e.g., Coligan, et al. (2000) Current Protocols in Protein Science, Vol. 2, John Wiley and Sons, Inc., New York; Ausubel, et al. (2001) Current Protocols in Molecular Biology, Vol. 3, John Wiley and Sons, Inc., NY, NY, pp. 16.0.5-16.22.17; Sigma-Aldrich, Co. (2001) Products for Life Science Research, St. Louis, MO; pp. 45-89; Amersham Pharmacia Biotech (2001) BioDirectory, Piscataway, N.J., pp. 384-391). Production, purification, and fragmentation of polyclonal and monoclonal antibodies are described (Coligan, et al. (2001) Current Protcols in Immunology, Vol. 1, John Wiley and Sons, Inc., New York; Harlow and Lane (1999) Using Antibodies, Cold Spring Harbor Laboratory Press, Cold Spring Harbor, NY; Harlow and Lane, supra). Standard techniques for characterizing ligand/receptor interactions are available (see, e.g., Coligan, et al. (2001) Current Protocols in Immunology, Vol. 4, John Wiley, Inc., New York).

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

What is claimed is:

1. A method for reducing soluble P-selectin in a patient with cancer comprising administering to the patient an effective amount of isoquercetin, vitamin B3, and vitamin C for a period of at least about 2 months; wherein the patient has been diagnosed with a cancer and is at an increased risk of bleeding; and exhibits an elevated level of soluble P-selectin prior to administration of isoquercetin, when compared to a reference or baseline level of soluble P-selectin; and wherein soluble p-selectin levels are reduced after administration of the effective amount of isoquercetin, vitamin B3, and vitamin C for a period of at least about 2 months.

2. A method for reducing or preventing formation of a thrombus in a patient with cancer comprising administering to the patient an effective amount of isoquercetin, vitamin B3, and vitamin C for a period of at least about 2 months; wherein the patient has been diagnosed with a cancer and is at an increased risk of bleeding; and exhibits an elevated level of soluble P-selectin prior to administration of isoquercetin, when compared to a reference or baseline level of soluble P-selectin; wherein the dose of isoquercetin is 500 mg per day wherein the patient does not exhibit primary venous thromboembolism (VTE) during treatment or after administration of the effective amount of isoquercetin, vitamin B3, and vitamin C for a period of at least about 2 months; and wherein soluble P-selectin is decreased at least about 30% when compared to a reference or baseline level of soluble P-selectin, following administration of the isoquercetin.

3. A method for promoting tumor regression in a patient with cancer comprising administering to the patient an effective amount of isoquercetin, vitamin B3, and vitamin C for a period of at least about 2 months; wherein the patient has been diagnosed with a cancer and is at an increased risk of bleeding; and exhibits an elevated level of soluble P-selectin prior to administration of isoquercetin, when compared to a reference or baseline level of soluble P-selectin; and wherein the patient exhibits tumor regression after administration of the effective amount of isoquercetin, vitamin B3, and vitamin C for a period of at least about 2 months.

4. A method for stabilizing or reducing metastatic cancer in a patient with cancer comprising administering to the patient an effective amount of isoquercetin, vitamin B3, and vitamin C for a period of at least about 2 months; wherein the patient has been diagnosed with a cancer and is at an increased risk of bleeding; and exhibits an elevated level of soluble P-selectin prior to administration of isoquercetin, when compared to a reference or baseline level of soluble P-selectin; and wherein administration results in stabilizing or reducing metastatic cancer in the patient after administration of the effective amount of isoquercetin, vitamin B3, and vitamin C for a period of at least about 2 months.

5. The method of claim 1, wherein soluble P-selectin decrease ranges from 30-40%, 40-50%, 55-60%, 60-70%, 70-75%, or 75-80% when compared to a reference or baseline level of soluble P-selectin, following administration of the isoquercetin.

6. The method of claim 1, wherein the wherein the cancer is metastatic cancer.

7. The method of claim 6, wherein the metastatic cancer is colorectal cancer, pancreatic cancer, or non-small cell lung cancer.

8. The method of claim 6, wherein the metastatic cancer is selected from the group consisting of metastasizing forms of Hodgkin lymphoma, colorectal cancer, cervical cancer, lung cancer, skin cancer such as squamous cell cancer or basal cell carcinoma, head and neck cancer, gastric cancer, and pancreatic cancer.

9. The method of claim 1, wherein the cancer is selected from the group consisting of estrogen receptor-dependent breast cancer, estrogen receptor-independent breast cancer, hormone receptor-dependent prostate cancer, hormone receptor-independent prostate cancer, brain cancer, renal cancer, glioblastoma, colon cancer, familial adenomatous polyposis (FAP), colorectal cancer, pancreatic cancer, bladder cancer, esophageal cancer, stomach cancer, genitourinary cancer, gastrointestinal cancer, uterine cancer, ovarian cancer, astrocytomas, gliomas, skin cancer, squamous cell carcinoma, Keratoakantoma, Bowen disease, cutaneous T-Cell Lymphoma, melanoma, basal cell carcinoma, actinic keratosis; ichtiosis; acne, acne vulgaris, sarcomas, Kaposi's sarcoma, osteosarcoma, head and neck cancer, small cell lung carcinoma, non-small cell lung carcinoma, leukemia, lymphomas and/or other blood cell cancers.

10. The method of claim 1, wherein the patient exhibits no severe adverse events (grade 3 or 4 toxicities) during treatment.

11. The method of claim 1, wherein the patient exhibits no VTE for at least 30-60 days following treatment.

12. The method of claim 1, wherein the patient exhibits no major hemorrhages during treatment.

13. The method of claim 1, wherein the patient exhibits a decrease in platelet-dependent thrombin generation of from about 30-60% when compared to a reference or baseline level of platelet dependent thrombin, following administration of the isoquercetin.

14. The method of claim 1, wherein the isoquercetin is administered in a composition comprising about 20 micrograms to about 3 grams of Vitamin B3, and optionally further comprises about 200 micrograms to about 3 grams of Vitamin C.

15. The method of claim 1, further comprising administering between about 1 000 micrograms to about 3 000 micrograms of folic acid.

16. The method of claim 2, further comprising administering between about 1 000 micrograms to about 3 000 micrograms of folic acid.

17. The method of claim 3, further comprising administering between about 1 000 micrograms to about 3 000 micrograms of folic acid.

18. The method of claim 4, further comprising administering between about 1 000 micrograms to about 3 000 micrograms of folic acid.

19. The method of claim 2, wherein the wherein the cancer is metastatic cancer.

20. The method of claim 19, wherein the metastatic cancer is colorectal cancer, pancreatic cancer, or non-small cell lung cancer.

21. The method of claim 19, wherein the metastatic cancer is selected from the group consisting of metastasizing forms of Hodgkin lymphoma, colorectal cancer, cervical cancer, lung cancer, skin cancer such as squamous cell cancer or basal cell carcinoma, head and neck cancer, gastric cancer, and pancreatic cancer.

22. The method of claim 2, wherein the cancer is selected from the group consisting of estrogen receptor-dependent breast cancer, estrogen receptor-independent breast cancer, hormone receptor-dependent prostate cancer, hormone receptor-independent prostate cancer, brain cancer, renal cancer, glioblastoma, colon cancer, familial adenomatous polyposis (FAP), colorectal cancer, pancreatic cancer, bladder cancer, esophageal cancer, stomach cancer, genitourinary cancer, gastrointestinal cancer, uterine cancer, ovarian cancer, astrocytomas, gliomas, skin cancer, squamous cell carcinoma, Keratoakantoma, Bowen disease, cutaneous T-Cell Lymphoma, melanoma, basal cell carcinoma, actinic keratosis; ichtiosis; acne, acne vulgaris, sarcomas, Kaposi's sarcoma, osteosarcoma, head and neck cancer, small cell lung carcinoma, non-small cell lung carcinoma, leukemia, lymphomas and/or other blood cell cancers.

23. The method of claim 3, wherein the wherein the cancer is metastatic cancer.

24. The method of claim 23, wherein the metastatic cancer is colorectal cancer, pancreatic cancer, or non-small cell lung cancer.

25. The method of claim 23, wherein the metastatic cancer is selected from the group consisting of metastasizing forms of Hodgkin lymphoma, colorectal cancer, cervical cancer, lung cancer, skin cancer such as squamous cell cancer or basal cell carcinoma, head and neck cancer, gastric cancer, and pancreatic cancer.

26. The method of claim 3, wherein the cancer is selected from the group consisting of estrogen receptor-dependent breast cancer, estrogen receptor-independent breast cancer, hormone receptor-dependent prostate cancer, hormone receptor-independent prostate cancer, brain cancer, renal cancer, glioblastoma, colon cancer, familial adenomatous polyposis (FAP), colorectal cancer, pancreatic cancer, bladder cancer, esophageal cancer, stomach cancer, genitourinary cancer, gastrointestinal cancer, uterine cancer, ovarian cancer, astrocytomas, gliomas, skin cancer, squamous cell carcinoma, Keratoakantoma, Bowen disease, cutaneous T-Cell Lymphoma, melanoma, basal cell carcinoma, actinic keratosis; ichtiosis; acne, acne vulgaris, sarcomas, Kaposi's sarcoma, osteosarcoma, head and neck cancer, small cell lung carcinoma, non-small cell lung carcinoma, leukemia, lymphomas and/or other blood cell cancers.

27. The method of claim 4, wherein the metastatic cancer is colorectal cancer, pancreatic cancer, or non-small cell lung cancer.

28. The method of claim 4, wherein the metastatic cancer is selected from the group consisting of metastasizing forms of Hodgkin lymphoma, colorectal cancer, cervical cancer, lung cancer, skin cancer such as squamous cell cancer or basal cell carcinoma, head and neck cancer, gastric cancer, and pancreatic cancer.

* * * * *